(12) United States Patent
Wakahoi et al.

(10) Patent No.: US 9,877,987 B2
(45) Date of Patent: Jan. 30, 2018

(54) ORALLY ADMINISTERED ADSORBENT, THERAPEUTIC AGENT FOR RENAL DISEASE, AND THERAPEUTIC AGENT FOR LIVER DISEASE

(71) Applicant: Kureha Corporation, Tokyo (JP)

(72) Inventors: Takashi Wakahoi, Tokyo (JP); Takahiro Akita, Tokyo (JP); Naohiro Sonobe, Tokyo (JP); Mieko Kuwahara, Tokyo (JP)

(73) Assignee: KUREHA CORPORATION, Tokyo (JP)

( * ) Notice: Subject to any disclaimer, the term of this patent is extended or adjusted under 35 U.S.C. 154(b) by 0 days.

(21) Appl. No.: 14/760,862

(22) PCT Filed: Feb. 24, 2014

(86) PCT No.: PCT/JP2014/054264
§ 371 (c)(1),
(2) Date: Jul. 14, 2015

(87) PCT Pub. No.: WO2014/129617
PCT Pub. Date: Aug. 28, 2014

(65) Prior Publication Data
US 2015/0342991 A1 Dec. 3, 2015

(30) Foreign Application Priority Data
Feb. 22, 2013 (JP) ................... 2013-033618

(51) Int. Cl.
*A61K 33/44* (2006.01)
*A61K 9/14* (2006.01)
*B01J 20/20* (2006.01)
*B01J 20/02* (2006.01)
*B01J 20/28* (2006.01)

(52) U.S. Cl.
CPC ............ *A61K 33/44* (2013.01); *A61K 9/14* (2013.01); *B01J 20/02* (2013.01); *B01J 20/20* (2013.01); *B01J 20/28016* (2013.01); *B01J 20/28064* (2013.01); *B01J 20/28066* (2013.01)

(58) Field of Classification Search
CPC .. A61K 33/44; A61K 9/14; B01J 20/20; B01J 20/28016; B01J 20/28064; B01J 20/28066; B01J 20/02
See application file for complete search history.

(56) References Cited

U.S. PATENT DOCUMENTS

| | | | |
|---|---|---|---|
| 4,681,764 A | 7/1987 | Endo et al. | |
| 6,300,276 B1 | 10/2001 | De Ruiter et al. | |
| 6,830,753 B2 | 12/2004 | Sonobe et al. | |
| 7,202,195 B2 | 4/2007 | Cannon et al. | |
| 7,651,974 B2 | 1/2010 | Sonobe et al. | |
| 8,309,130 B2 | 11/2012 | Sonobe et al. | |
| 8,357,366 B2 | 1/2013 | Sonobe et al. | |
| 8,440,228 B2 | 5/2013 | Sonobe et al. | |
| 8,865,161 B2 | 10/2014 | Sonobe et al. | |
| 8,920,796 B2 | 12/2014 | Sonobe et al. | |
| 2005/0079167 A1 | 4/2005 | Sonobe et al. | |
| 2005/0112114 A1 | 5/2005 | Sonobe et al. | |
| 2007/0270307 A1 | 11/2007 | Hamasaki et al. | |
| 2008/0031972 A1 | 2/2008 | Sonobe et al. | |
| 2008/0044477 A1 | 2/2008 | Sonobe et al. | |
| 2008/0081073 A1 | 4/2008 | Sonobe et al. | |
| 2009/0181095 A1 | 7/2009 | Goto et al. | |
| 2012/0244195 A1 | 9/2012 | Sonobe et al. | |
| 2013/0171206 A1 | 7/2013 | Sonobe et al. | |
| 2013/0202664 A1 | 8/2013 | Kurokawa et al. | |
| 2013/0344147 A1 | 12/2013 | Kainose et al. | |

FOREIGN PATENT DOCUMENTS

| | | |
|---|---|---|
| CN | 1488360 A | 4/2004 |
| CN | 1615908 A | 5/2005 |
| CN | 1691948 A | 11/2005 |
| CN | 1691949 A | 11/2005 |
| CN | 1938037 A | 3/2007 |
| CN | 1938226 A | 3/2007 |
| CN | 1942196 A | 4/2007 |
| CN | 101904867 A | 12/2010 |
| EP | 1547605 A1 | 6/2005 |
| EP | 1745792 A1 | 1/2007 |
| EP | 2628483 A1 | 9/2013 |
| EP | 2684561 A1 | 1/2014 |

(Continued)

OTHER PUBLICATIONS

International Search Report of PCT/JP2014/054264 dated Apr. 15, 2014.
Boki, K, Removal by Adsorption of Hydrogen Sulfide by a New Type of Activated Carbon Containing Nitrogen, Japanese Journal of Hygiene, 1983, vol. 38, No. 5, p. 877-882.
Notification of the First Office Action dated Sep. 1, 2016, in Chinese Patent Application No. 201480007073.1, with English translation.
Notification of Reason for Refusal dated Aug. 22, 2016, in Korean Patent Application No. 10-2015-7023926, with English translation.
Office Action dated Oct. 28, 2016, in Canadian Patent Application No. 2,897,937.
Notice of Decision Application No. of Refusal issued Feb. 20, 2017, in Korean Patent Application No. 10-2015-7023926, with English translation.
Bosoi et al., "AST-120 (Spherical Carbon Adsorbent) Lowers Ammonia Levels and Attenuates Brain Edema in Bile Duct-Ligated Rats," Hepatology, vol. 53, No. 6, 2011, pp. 1995-2002, (Continued)

*Primary Examiner* — Suzanne Ziska
*Assistant Examiner* — Thurman Wheeler
(74) *Attorney, Agent, or Firm* — Birch, Stewart, Kolasch & Birch, LLP

(57) ABSTRACT

An object of the present invention is to provide spherical activated carbon exhibiting excellent adsorption ability for uremic substances in the body, and particularly for -aminoisobutyric acid. Accordingly, provided is an orally administered adsorbent comprising spherical activated carbon containing not less than 0.5 wt % of nitrogen atoms, having a specific surface area determined by the Brunauer-Emmett-Teller (BET) method of 700 $m^2$/g to 3000 $m^2$, and having an average particle size from 0.01 to 1 mm.

7 Claims, 4 Drawing Sheets

(56) References Cited

FOREIGN PATENT DOCUMENTS

| | | | |
|---|---|---|---|
| JP | S6211611 B2 | | 3/1987 |
| JP | 11-116648 A | | 4/1999 |
| JP | 2001-114852 A | | 4/2001 |
| JP | 2004168587 | * | 6/2004 |
| JP | 2004168587 A | | 6/2004 |
| JP | 2005314416 A | | 11/2005 |
| JP | 2006015334 A | | 1/2006 |
| JP | 2006131461 A | | 5/2006 |
| JP | 2008-120856 A | | 5/2008 |
| JP | 2009056449 A | | 3/2009 |
| JP | 5390709 | * | 11/2009 |
| JP | 5390790 | * | 11/2009 |
| JP | 2009269765 A | | 11/2009 |
| JP | 2011037749 A | | 2/2011 |
| JP | 2012102072 A | | 5/2012 |
| KP | 2006-0135011 A | | 12/2006 |
| KR | 1020060135012 A | | 12/2006 |
| RU | 2375302 C2 | | 12/2009 |
| RU | 2396964 C2 | | 8/2010 |
| RU | 2396965 C2 | | 8/2010 |
| WO | WO2005094844 A1 | | 10/2005 |
| WO | WO 2005094845 A1 | | 10/2005 |
| WO | WO 2005095276 A1 | | 10/2005 |
| WO | WO 2008152994 A1 | | 12/2008 |
| WO | WO 2010001485 A1 | | 1/2010 |
| WO | WO 2010/104056 A1 | | 9/2010 |
| WO | WO 2012050025 A1 | | 4/2012 |
| WO | WO 2012121202 A1 | | 9/2012 |

OTHER PUBLICATIONS

Canadian Intellectual Property Office, "Notice of a Requisition by the Examiner in accordance with Subsection 30(2) of the Patent Rules," issued in connection with Canadian Patent Application No. 2,897,937, dated Jul. 18, 2017.
Canadian Intellectual Property Office, "Notice of a Requisition by the Examiner in accordance with Subsection 30(2) of the Patent Rules," issued in connection with Canadian Patent Application No. 2,897,944, dated Jul. 12, 2017.
Canadian Intellectual Property Office, "Notice of a Requisition by the Examiner in accordance with Subsection 30(2) of the Patent Rules," issued in connection with Canadian Patent Application No. 2,897,944, dated Nov. 1, 2016.
European Patent Office, "Communication with Extended European Search Report," issued in connection with European Patent Application No. 14753926.6, dated Jul. 1, 2016.
European Patent Office, "Communication with Extended European Search Report," issued in connection with European Patent Application No. 14754624.6, dated Oct. 26, 2016.
European Patent Office, "Communication with Extended European Search Report," issued in connection with European Patent Application No. 14754829.1, dated Jul. 1, 2016.
International Searching Authority, "International Search Report," issued in connection with PCT/JP2014/054261, dated Apr. 15, 2014.
International Searching Authority, "International Search Report," issued in connection with PCT/JP2014/054262, dated Apr. 15, 2014.
International Searching Authority, "International Search Report," issued in connection with PCT/JP2014/054265, dated Apr. 15, 2014.
Japanese Patent Office, "Notification of Reasons for Rejection," issued in connection with Japanese Patent Application No. 2015-501527, dated Jul. 18, 2017.
Japanese Patent Office, "Notification of Reasons for Rejection," issued in connection with Japanese Patent Application No. 2015-501528, dated Jul. 25, 2017.
Japanese Patent Office, "Notification of Reasons for Rejection," issued in connection with Japanese Patent Application No. 2015-501530, dated Jul. 25, 2017.
Japanese Patent Office, "Notification of Reasons for Rejection," issued in connection with Japanese Patent Application No. 2015-501531, dated Jul. 25, 2017.

Korean Intellectual Property Office, "Notification of Decision of Refusal," issued in connection with Korean Patent Application No. 10-2015-7024219, dated Mar. 16, 2017.
Korean Intellectual Property Office, "Notification of Reason for Refusal," issued in connection with Korean Patent Application No. 10-2015-7024219, dated Sep. 1, 2016.
Leong et al, "Indoxyl Sulfate-Review of Toxicity and Therapeutic Strategies," Toxins, vol. 8, No. 358, 2016, pp. 1-13.
Miyazaki et al., "Uremic Toxins," The Japanese Journal of Clinical Dialysis, vol. 14, No. 4, 1998, pp. 433-438.
Niwa et al., "Effect of Oral Sorbent, AST-120, on Serum Concentration of Indoxyl Sulfate in Uremic Rats," The Japanese Journal of Nephrology, XXXII(6), 1990, pp. 695-701.
Quantachrome Instruments, "Micropore Size Calculations," pp. 1-104 (2004-2006).
Russian Patent Office, "Request of the Substantive Examination," issued in connection with Russian Patent Application No. 2015137937/15(058164), dated Apr. 14, 2017.
Sevilla et al., "Preparation and Hydrogen Storage Capacity of Highly Porous Activated Carbon Materials Derived from Polythiophene," International Journal of Hydrogen Energy, vol. 36, 2011, pp. 15658-15663.
Sevilla et al., "Ultrahigh Surface Area Polypyrrole-Based Carbons with Superior Performance for Hydrogen Storage," Energy & Environment Science, vol. 4, 2011, pp. 2930-2936.
Taiwanese Patent Office, "Decision of the Intellectual Property Office," issued in connection with Taiwanese Patent Application No. 103105936, dated Apr. 19, 2016.
Taiwanese Patent Office, "Office Action of the Intellectual Property Office," issued in connection with Taiwanese Patent Application No. 103105936, dated Nov. 17, 2016.
The State Intellectual Property Office of the People's Republic of China, "Notification of the First Office Action," issued in connection with Chinese Patent Application No. 201480007257.8, dated Sep. 21, 2016.
The State Intellectual Property Office of the People's Republic of China, "Second Office Action," issued in connection with Chinese Patent Application No. 201480007257.8, dated Apr. 27, 2017.
U.S. Patent and Trademark Office, "Advisory Action," issued in connection with U.S. Appl. No. 14/767,971, dated Jul. 8, 2016.
U.S. Patent and Trademark Office, "Final Office Action," issued in connection with U.S. Appl. No. 14/760,879, dated Dec. 14, 2016.
U.S. Patent and Trademark Office, "Final Office Action," issued in connection with U.S. Appl. No. 14/767,971, dated Feb. 17, 2017.
U.S. Patent and Trademark Office, "Final Office Action," issued in connection with U.S. Appl. No. 14/767,971, dated Mar. 31, 2016.
U.S. Patent and Trademark Office, "Final Office Action," issued in connection with U.S. Appl. No. 14/768,580, dated Oct. 7, 2016.
U.S. Patent and Trademark Office, "Non-Final Office Action," issued in connection with U.S. Appl. No. 14/760,879, dated Jul. 21, 2016.
U.S. Patent and Trademark Office, "Non-Final Office Action," issued in connection with U.S. Appl. No. 14/760,879, dated May 15, 2017.
U.S. Patent and Trademark Office, "Non-Final Office Action," issued in connection with U.S. Appl. No. 14/767,971, dated Aug. 23, 2016.
U.S. Patent and Trademark Office, "Non-Final Office Action," issued in connection with U.S. Appl. No. 14/767,971, dated Nov. 13, 2015.
U.S. Patent and Trademark Office, "Non-Final Office Action," issued in connection with U.S. Appl. No. 14/768,580, dated May 11, 2016.
U.S. Patent and Trademark Office, "Non-Final Office Action," issued in connection with U.S. Appl. No. 15/426,367, dated Apr. 19, 2017.
Extended European Search Report dated Jul. 5, 2016, in European Patent Application No. 14754689.9.
Notice of Decision of Refusal dated Apr. 26, 2017, in Korean Patent Application No. 10-2015-7023926, with English translation.
Notice Regarding Submission of Third Party Information Disclosure Statement dated Apr. 25, 2017, in Japanese Patent Application No. 2015-501530, with English translation.

(56) References Cited

OTHER PUBLICATIONS

Notification of Reason for Refusal dated Jun. 1, 2017, in Korean Patent Application No. 10-2017-7007990, with English translation.
Second Office Action dated Apr. 12, 2017, in Chinese Patent Application No. 201480007073.1, with English translation.
Russian Office Action and Search Report dated in Russian Application No. 2015139365 Mar. 7, 2017, together with an English translation thereof.
Chinese Office Action, dated Nov. 9, 2017, for Chinese Application No. 201480007073.1 with English translation.
European Office Action, dated Oct. 30, 2017, for European Application No. 14754689.9.

* cited by examiner

US 9,877,987 B2

ORALLY ADMINISTERED ADSORBENT, THERAPEUTIC AGENT FOR RENAL DISEASE, AND THERAPEUTIC AGENT FOR LIVER DISEASE

TECHNICAL FIELD

The present invention relates to an orally administered adsorbent comprising spherical activated carbon containing not less than 0.5 wt % nitrogen atoms. The present invention also relates to a therapeutic or prophylactic agent for a renal disease and a therapeutic or prophylactic agent for a hepatic disease that contain as an active ingredient the aforementioned orally administered adsorbent.

The orally administered adsorbent according to the present invention has excellent adsorption ability for uremic substances in the body, particularly -aminoisobutyric acid.

BACKGROUND ART

Accompanying organ functional impairment in patients deficient in renal function or hepatic function, poisonous toxins accumulate and are produced in the body such as in the blood, and cause uremia or encephalopathy such as impaired consciousness. Since the number of such patients has shown an increasing trend year by year, the development of therapeutic medicines or organ substitute devices that has the function of removing toxins to outside the body in place of these deficient organs is a critical topic. Removal of poisonous substances by hemodialysis is currently the method most widely used as artificial kidneys. However, such hemodialysis-type artificial kidneys are not necessarily satisfactory due to problems such as the necessity for a specialized technician from the viewpoint of safety management because a special machine is used, and additionally, the high physical, mental and economic burden on the patient due to extracorporeal removal of blood, and the like.

As a means for solving these problems, an oral adsorbent that can be orally ingested and can treat functional impairment of the kidney or liver has been developed and used (Patent Document 1). The oral adsorbent has been widely clinically used in, for example, patients with hepatorenal functional impairment as an oral therapeutic agent that has fewer adverse effects such as constipation. The oral adsorbent contains a porous spherical carbonaceous substance (that is, spherical activated carbon) having a certain functional group, has excellent adsorbance of poisonous substances (that is, -aminoisobutyric acid, □-amino-n-butyric acid, dimethylamine, and octopamine) in the presence of bile acid in the intestines, and also has beneficial selective adsorbance in the sense that it adsorbs little of the beneficial components in the intestines such as digestive enzymes and the like. Furthermore, the adsorbent described in Patent Document 1 uses pitch such as petroleum pitch as a carbon source, and is produced by performing oxidation treatment and reduction treatment after preparation of the spherical activated carbon. The spherical activated carbon that has undergone this oxidation treatment and reduction treatment has been named surface-modified spherical activated carbon.

Additionally, Patent Document 2 discloses that surface-modified spherical activated carbon having an average particle size from 50 µm to 200 µm has excellent initial adsorption ability. That is, in the general residence time (within 3 hours) in the upper small intestine after ingestion of an orally administered adsorbent, it can very rapidly adsorb poisonous toxins (particularly -aminoisobutyric acid) in the body.

CITATION LIST

Patent Literature

Patent Document 1: Japanese Examined Patent Application Publication No. S62-11611B
Patent Document 2: Japanese Unexamined Patent Application Publication No. 2005-314416A

SUMMARY OF INVENTION

Technical Problem

The above surface-modified spherical activated carbons described in Patent Documents 1 and 2 have excellent adsorption ability for uremic substances in the body, particularly -aminoisobutyric acid. However, even the adsorption ability for uremic substances of the surface-modified spherical activated carbon described in Patent Documents 1 and 2 is insufficient, and further improvement has been anticipated. An object of the present invention is to provide spherical activated carbon exhibiting excellent adsorption ability for uremic substances in the body, and particularly for -aminoisobutyric acid.

Solution to Problem

As a result of diligent research on spherical activated carbon having excellent adsorption ability for uremic substances in the body, the present inventors unexpectedly discovered that spherical activated carbon containing not less than 0.5 wt % nitrogen atoms exhibits excellent adsorption ability for uremic substances, particularly adsorption ability for -aminoisobutyric acid. As the nitrogen atom quantity increases, the spherical activated carbon has markedly increased adsorption ability for -aminoisobutyric acid, and it is surprising that nitrogen atoms of spherical activated carbon are related to adsorption ability for uremic substances.

The present invention is based on such knowledge.
Therefore, the present invention relates to the following.
[1] An orally administered adsorbent comprising spherical activated carbon containing not less than 0.5 wt % nitrogen atoms, having a specific surface area determined by the Brunauer-Emmett-Teller (BET) method from 700 $m^2/g$ to 3000 $m^2/g$, and having an average particle size from 0.01 mm to 1 mm;
[2] The orally administered adsorbent according to [1], wherein the average particle size of the spherical activated carbon is from 50 to 200 µm;
[3] The orally administered adsorbent according to [1] or [2], wherein the spherical activated carbon is prepared using a thermoplastic resin, thermosetting resin, or ion exchange resin containing nitrogen atoms as a carbon source;
[4] The orally administered adsorbent according to [3], wherein the thermoplastic resin or ion exchange resin contains a monomer selected from the group consisting of acrylonitrile, ethylacrylonitrile, methylacrylonitrile, diphenylacrylonitrile, and chloroacrylonitrile;
[5] The orally administered adsorbent according to [3], wherein the thermosetting resin contains a monomer selected from the group consisting of melamine and urea;

[6] A therapeutic or prophylactic agent for a renal disease containing as an active ingredient the orally administered adsorbent described in any one of [1] to [5]; and

[7] A therapeutic or prophylactic agent for a hepatic disease containing as an active ingredient the orally administered adsorbent described in any one of [1] to [5]. Furthermore, the present specification discloses the following.

[8] A method of prophylaxis or therapy of a renal disease or a hepatic disease wherein the orally administered adsorbent described in any one of [1] to [5] is administered in an effective dose to a renal disease or hepatic disease therapy subject;

[9] Spherical activated carbon for use in (a) therapy (method) of a renal disease or a hepatic disease, the spherical activated carbon containing not less than 0.5 wt % nitrogen atoms, having a specific surface area determined by the BET method from 700 $m^2/g$ to 3000 $m^2/g$, and having an average particle size from 0.01 mm to 1 mm;

[10] The spherical activated carbon according to [9], wherein the average particle size of the spherical activated carbon is from 50 to 200 μm;

[11] The spherical activated carbon according to [9] or [10], wherein the spherical activated carbon is prepared using a thermoplastic resin, thermosetting resin, or ion exchange resin containing nitrogen atoms as a carbon source;

[12] The spherical activated carbon according to [11], wherein the thermoplastic resin or ion exchange resin contains a monomer selected from the group consisting of acrylonitrile, ethylacrylonitrile, methylacrylonitrile, diphenylacrylonitrile, and chloroacrylonitrile;

[13] The spherical activated carbon according to [11], wherein the thermosetting resin contains a monomer selected from the group consisting of melamine and urea;

[14] Use of spherical activated carbon for production of a prophylactic or therapeutic medicine for a renal disease or a hepatic disease, the spherical activated carbon containing not less than 0.5 wt % nitrogen atoms, having a specific surface area determined by the BET method from 700 $m^2/g$ to 3000 $m^2/g$, and having an average particle size from 0.01 mm to 1 mm;

[15] Use of the spherical activated carbon according to [14], wherein the average particle size of the spherical activated carbon is from 50 to 200 μm;

[16] Use of the spherical activated carbon according to [14] or [15], wherein the spherical activated carbon is prepared using a thermoplastic resin, thermosetting resin, or ion exchange resin containing nitrogen atoms as a carbon source;

[17] Use of the spherical activated carbon according to [16], wherein the spherical activated carbon is prepared using a thermoplastic resin, thermosetting resin, or ion exchange resin containing nitrogen atoms as a carbon source;

[18] Use of the spherical activated carbon according to [16], wherein the thermosetting resin contains a monomer selected from the group consisting of melamine and urea;

[19] Use of spherical activated carbon for prophylaxis or therapy of a renal disease or a hepatic disease, the spherical activated carbon containing not less than 0.5 wt % nitrogen atoms, having a specific surface area determined by the BET method from 700 $m^2/g$ to 3000 $m^2/g$, and having an average particle size from 0.01 mm to 1 mm;

[20] Use of the spherical activated carbon according to [19], wherein the average particle size of the spherical activated carbon is from 50 to 200 μm;

[21] Use of the spherical activated carbon according to [19] or [20], wherein the spherical activated carbon is prepared using a thermoplastic resin, thermosetting resin, or ion exchange resin containing nitrogen atoms as a carbon source;

[22] Use of the spherical activated carbon according to [21], wherein the spherical activated carbon is prepared using a thermoplastic resin, thermosetting resin, or ion exchange resin containing nitrogen atoms as a carbon source; and

[23] Use of the spherical activated carbon according to [21], wherein the thermosetting resin contains a monomer selected from the group consisting of melamine and urea.

Advantageous Effects of Invention

According to the orally administered adsorbent of the present invention, because adsorption ability for uremic substances, particularly adsorption ability for -aminoisobutyric acid, is remarkably excellent, a large quantity of poisonous toxins can be adsorbed by a small quantity of orally administered adsorbent. Therefore, higher efficacy can be obtained by ingestion of the same quantity as a conventional orally administered adsorbent. Alternatively, the dosage for obtaining the same efficacy can be reduced from the dosage of a conventional orally administered adsorbent.

DESCRIPTION OF EMBODIMENTS

[1] Orally Administered Adsorbent

The spherical activated carbon used for the orally administered adsorbent of the present invention contains not less than 0.5 wt % nitrogen atoms, has a specific surface area determined by the BET method from 700 $m^2/g$ to 3000 $m^2/g$, and has an average particle size from 0.01 mm to 1 mm.

(Nitrogen Atom Quantity)

The nitrogen atom content of the spherical activated carbon is not less than 0.5 wt %, preferably not less than 0.7 wt %, more preferably not less than 0.9 wt %, even more preferably 0.95 wt %, and even more preferably not less than 1.0 wt %. When the nitrogen atom content is not less than 0.5 wt %, the rise in adsorption ability for uremic substances is remarkable, which is desirable. The upper limit of nitrogen atom content is not particularly limited, but not greater than 20 wt % is preferred. When the nitrogen atom content is not less than 0.5 wt %, the -aminoisobutyric acid adsorbed quantity increases as nitrogen content increases.

Figure 2:
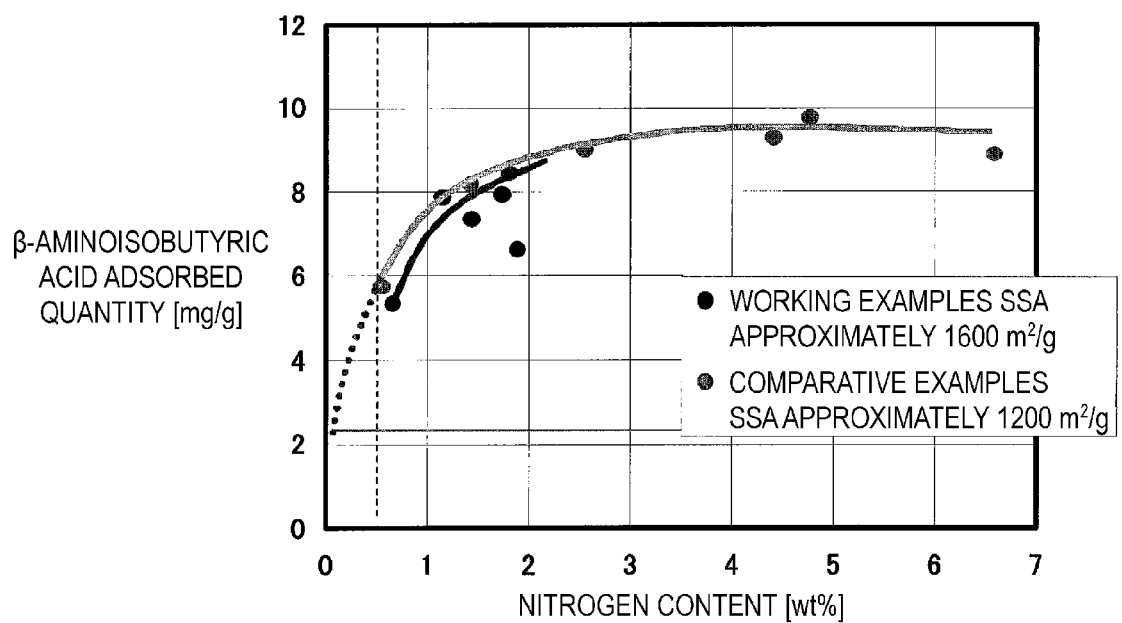
FIG. 2 is a graph showing the relationship between nitrogen content and -aminoisobutyric acid adsorbed quantity (24 hours) for working examples having a BET specific surface area of approximately 1600 $m^2/g$ (Working Examples 2, 3, 4, 5, and 6) and working examples having a BET specific surface area of approximately 1200 $m^2/g$ (Working Examples 1, 7, 8, 9, 13, 16, and 17).

The -aminoisobutyric acid adsorbed quantity is also influenced by a specific surface area. FIG. 2 illustrates the relationship between nitrogen content and -aminoisobutyric acid adsorbed quantity (24 hours) for spherical activated carbon having a BET specific surface area of approximately 1600 m$^2$/g (Working Examples 2, 3, 4, 5, and 6) and spherical activated carbon having a BET specific surface area of approximately 1200 m$^2$/g (Working Examples 1, 7, 8, 9, 13, 16, and 17). As is clear from FIG. 2, as the nitrogen content increased, the -aminoisobutyric acid adsorbed quantity increased. In particular, when the nitrogen content was from 0.5 wt % to 3 wt %, a striking correlation between nitrogen content and -aminoisobutyric acid adsorbed quantity was seen.

(Carbon Source)

The carbon source of the spherical activated carbon is not particularly limited provided that it contains nitrogen atoms, but examples include heat-fusible resins and heat-infusible resins.

(Heat-Fusible Resin)

Examples of heat-fusible resins include thermoplastic resins containing nitrogen atoms produced using a monomer containing nitrogen atoms (for example, crosslinked vinyl resin containing nitrogen atoms).

Examples of monomers containing nitrogen atoms for producing crosslinked vinyl resin containing nitrogen atoms include acrylonitrile, methylacrylonitrile (2-methylacrylonitrile), ethylacrylonitrile (for example, 2-hydroxyethylacrylonitrile, 2-(1-hydroxyethyl)acrylonitrile, 2-(2-fluoroethyl) acrylonitrile), diphenylacrylonitrile (for example, 2,3-diphenylacrylonitrile, 3,3-diphenylacrylonitrile), and chloroacrylonitrile (2-chloroacrylonitrile). A vinyl resin of a polymer of only these monomers containing nitrogen atoms, or a crosslinked vinyl resin of a copolymer with other monomers may be used.

The above crosslinked vinyl resins used as a carbon source may be a spherical polymer obtained by emulsion polymerization, bulk polymerization, or solution polymerization, or, preferably, a spherical polymer obtained by suspension polymerization. To make the spherical crosslinked vinyl resin uniformly infusible, it is necessary to form pores in the crosslinked vinyl resin in advance. Pores may be formed in the resin by adding a porogen at the time of polymerization. The BET specific surface area of the crosslinked vinyl resin required to make the crosslinked vinyl resin infusible is preferably not less than 5 m$^2$/g, and more preferably not less than 10 m$^2$/g. For example, when preparing a crosslinked vinyl resin by suspension polymerization, a spherical crosslinked vinyl resin may be prepared by adding an organic phase containing a vinyl-based monomer, a crosslinking agent, a porogen, and a polymerization initiator to an aqueous dispersion medium containing a dispersion stabilizer, and after forming numerous organic droplets suspended in an aqueous phase by agitating to mix, and heating them to polymerize the monomer in the organic droplets.

As other monomers that form a copolymer with the above monomer containing nitrogen atoms, any vinyl-based monomer that can be formed into spheres can be used, examples of which include aromatic vinyl-based monomers such as styrene and styrene derivatives in which a vinyl group hydrogen or phenyl group hydrogen is substituted, and compounds in which a heterocyclic or polycyclic compound is bonded to a vinyl group instead of a phenyl group. More specific examples of aromatic vinyl-based monomers include □- or -methylstyrene, □- or -ethylstyrene, methoxystyrene, phenylstyrene, chlorostyrene, and the like, and o-, m-, or p-methylstyrene, ethylstyrene, methoxystyrene, methylsilylstyrene, hydroxystyrene, chlorostyrene, cyanostyrene, nitrostyrene, aminostyrene, and carboxystyrene, and sulfoxystyrene, sodium styrene sulfonate, and the like, and vinylpyridine, vinylthiophene, vinylpyrrolidone, vinylnaphthalene, vinylanthracene, vinylbiphenyl, and the like. Aliphatic vinyl-based monomers may also be used, specific examples of which include vinyl esters such as ethylene, propylene, isobutylene, diisobutylene, vinyl chloride, acrylic acid ester, methacrylic acid ester, vinyl acetate, and the like, vinyl ketones such as vinyl methyl ketone, vinyl ethyl ketone, and the like, vinyl aldehydes such as acrolein, methacrolein, and the like, and vinyl ethers such as vinyl methyl ether, vinyl ethyl ether, and the like. A crosslinked vinyl resin with a monomer containing nitrogen atoms may be prepared using one or more of these vinyl-based monomers, but methylstyrenes (□-methylstyrene, -methylstyrene, o-methylstyrene, m-methylstyrene, and p-methylstyrene), ethylstyrenes (□-ethylstyrene and -ethylstyrene), and styrene are preferred.

As the crosslinking agent, any crosslinking agent that can be used to crosslink the aforementioned vinyl-based monomers may be used, examples of which include divinylbenzene, divinylpyridine, divinyltoluene, divinylnaphthalene, diallyl phthalate, ethylene glycol diacrylate, ethylene glycol dimethylate, divinylxylene, divinylethylbenzene, divinylsulfone, and polyvinyl or polyallyl ethers of glycol or glycerol, polyvinyl or polyallyl ethers of pentaerythritol, polyvinyl or polyallyl ethers of mono or dithio derivatives of glycol, and polyvinyl or polyallyl ethers of resorcinol, and divinyl ketone, divinyl sulfide, allyl acrylate, diallyl maleate, diallyl fumarate, diallyl succinate, diallyl carbonate, diallyl malonate, diallyl oxalate, diallyl adipate, diallyl sebacate, triallyl tricarballylate, triallyl aconitate, triallyl citrate, triallyl phosphate, N,N'-methylenediacrylamide, 1,2-di(□-methylmethylenesulfonamide)ethylene, trivinylbenzene, trivinylnaphthalene, polyvinylanthracene, and trivinylcyclohexane. Particularly preferred crosslinking agents include polyvinyl aromatic hydrocarbons (for example, divinylbenzene), glycol trimethacrylates (for example, ethylene glycol dimethacrylate), and polyvinyl hydrocarbons (for example, trivinylcyclohexane). Divinylbenzene is most preferred due to its excellent pyrolysis characteristics.

Examples of suitable porogens include alkanols having from 4 to 10 carbons (for example, n-butanol, sec-butanol, 2-ethylhexanol, decanol, and 4-methyl-2-pentanol), alkyl esters having at least 7 carbons (for example, n-hexyl acetate, 2-ethylhexyl acetate, methyl oleate, dibutyl sebacate, dibutyl adipate, and dibutyl carbonate), alkyl ketones having from 4 to 10 carbons (for example, dibutyl ketone and methyl isopropyl ketone), alkyl carboxylates (for example, heptanoic acid), aromatic hydrocarbons (for example, toluene, xylene, and benzene), higher saturated aliphatic hydrocarbons (for example, hexane, heptane, and isooctane), and cyclic aliphatic hydrocarbons (for example, cyclohexane).

The polymerization initiator is not particularly limited, and one that is generally used in this field may be used, but an oil-soluble polymerization initiator that is soluble in the polymerizable monomer is preferred. Examples of the polymerization initiator include dialkyl peroxides, diacyl peroxides, peroxyesters, peroxydicarbonates, and azo compounds. More specific examples include dialkyl peroxides such as methyl ethyl peroxide, di-t-butyl peroxide, and dicumyl peroxide; diacyl peroxides such as isobutyl peroxide, benzoyl peroxide, 2,4-dicyclobenzoyl peroxide, and 3,5,5-trimethylhexanoyl peroxide; peroxyesters such as t-butyl peroxypivalate, t-hexyl peroxypivalate, t-butyl peroxyneodecanoate, t-hexyl peroxyneodecanoate, 1-cyclohexyl-1-methylethyl peroxyneodecanoate, 1,1,3,3-tetramethylbutyl peroxyneodecanoate, cumyl peroxyneodecanoate, and (☐,☐-bis-neodecanoylperoxyθ) diisopropylbenzene; peroxydicarbonates such as bis(4-t-butylcyclohexyl)peroxydicarbonate, di-n-propyl-oxydicarbonate, diisopropyl peroxydicarbonate, di(2-ethylethylperoxy) dicarbonate, dimethoxybutyl peroxydicarbonate, and di(3-methyl-3-methoxybutylperoxy)dicarbonate; and azo compounds such as 2,2'-azobisisobutyronitrile, 2,2'-azobis (4-methoxy-2,4-dimethylvaleronitrile), 2,2'-azobis(2,4-dimethylvaleronitrile), and 1,1'-azobis(1-cyclohexanecarbonitrile); and the like.

(Heat-Infusible Resin)

The heat-infusible resin used in the present invention is not limited provided that it contains nitrogen atoms, but specific examples of which include thermosetting resins containing nitrogen atoms (for example, melamine resin and urea resin) and ion exchange resins containing nitrogen atoms.

(Melamine Resin)

Melamine resin is a thermosetting resin categorized as an amino resin, and is produced by polycondensation of melamine and formaldehyde. Specifically, the starting material used is methylol melamine obtained by condensing melamine and formaldehyde under alkaline conditions. Heating the methylol melamine causes polycondensation, resulting in a thermosetting resin crosslinked in a mesh pattern.

Furthermore, melamine resin alone may be used as the melamine resin. Additionally, a resin of a copolymer of melamine resin with urea, phenol, or the like may be used.

(Urea Resin)

Urea resin is produced by polycondensation of urea and formaldehyde. Specifically, urea and formaldehyde undergo a dehydration condensation reaction under alkaline conditions or acidic conditions to obtain a condensate. Urea resin alone may also be used as the urea resin. Additionally, a resin of a copolymer of melamine resin with polyurethane, urea, phenol, or the like may be used.

(Ion Exchange Resin Containing Nitrogen Atoms)

The ion exchange resin containing nitrogen atoms is not limited, but an ion exchange resin having a structure in which an ion exchange group is bonded to a copolymer matrix having a three-dimensional mesh skeleton of crosslinked vinyl resin containing nitrogen atoms may be used. Depending on the ion exchange group, ion exchange resins are broadly classified into strongly acidic ion exchange resins having a sulfonic acid group, weakly acidic ion exchange resins having a carboxylic acid group or sulfonic acid group, strongly basic ion exchange resins having a quaternary ammonium salt, and weakly basic ion exchange resins having a primary or tertiary amine. Other special resins include so-called hybrid ion exchange resins having ion exchange groups of both an acid and a base. In the present invention, all of these ion exchange resins containing nitrogen atoms may be used as a carbon source.

(Diameter)

The diameter of the spherical activated carbon used for the orally administered adsorbent according to the present invention is not particularly limited, but is preferably from 0.005 to 1.5 mm, more preferably from 0.01 to 1 mm, and even more preferably from 0.02 to 0.8 mm. When the diameter of the spherical activated carbon is less than 0.005 mm, the exterior surface area of the spherical activated carbon increases and adsorption of beneficial substances such as digestive enzymes readily occurs, which is undesirable. When the diameter exceeds 1.5 mm, the diffusion length of toxins into the spherical activated carbon increases and the adsorption rate decreases, which is undesirable.

(Average Particle Size)

The particle diameter at a cumulative particle size percentage of 50% on a volume standard cumulative particle size distribution curve created using a laser diffraction-style particle size distribution analyzer is used as the average particle size (Dv50). The range of average particle size of the spherical activated carbon used for the orally administered adsorbent according to the present invention is not particularly limited provided that the average particle size is from 0.01 to 1 mm (from 10 μm to 1000 μm). When the average particle size of the spherical activated carbon is less than 0.01 mm, the exterior surface area of the spherical activated carbon increases and adsorption of beneficial substances such as digestive enzymes readily occurs, which is undesirable. When the average particle size exceeds 1 mm, the diffusion length of toxins into the spherical activated carbon increases and the adsorption rate decreases, which is undesirable. The average particle size is preferably from 20 μm to 800 μm, and more preferably from 30 μm to 500 μm. In particular, spherical activated carbon having an average particle size from 50 to 200 μm is most preferred because it has excellent initial adsorption ability, and in the general residence time in the upper small intestine, it can very rapidly adsorb poisonous toxins or precursors thereof (for example, DL- -aminoisobutyric acid) in the body.

Figure 4:
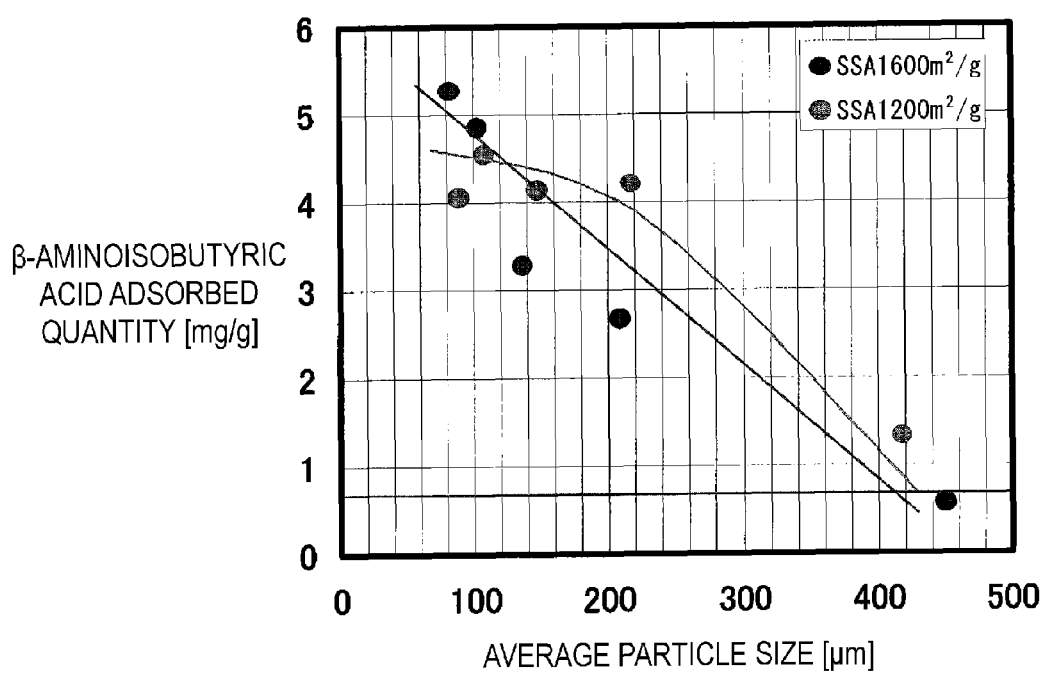
FIG. 4 is a graph showing the relationship between an average particle size and -aminoisobutyric acid adsorbed quantity (3 hours) for working examples having a BET specific surface area of approximately 1600 $m^2/g$ (Working Examples 4, 20, 21, 22, and 23) and working examples having a BET specific surface area of approximately 1200 $m^2/g$ (Working Examples 17, 24, 25, 26, and 27).

FIG. 4 illustrates the relationship between average particle size and -aminoisobutyric acid adsorbed quantity (3 hours) for spherical activated carbon having a BET specific surface area of approximately 1600 $m^2/g$ (Working Examples 4, 20, 21, 22, and 23) and spherical activated carbon having a BET specific surface area of approximately 1200 $m^2/g$ (Working Examples 17, 24, 25, 26, and 27). As is clear from FIG. 4, when average particle size was from 50 to 200 μm, -aminoisobutyric acid adsorbed quantity (3 hours) increased. Specifically, when the average particle size is from 50 to 200 μm, the initial adsorption ability in the body is excellent, which is desirable.

(Specific Surface Area)

Figure 3:
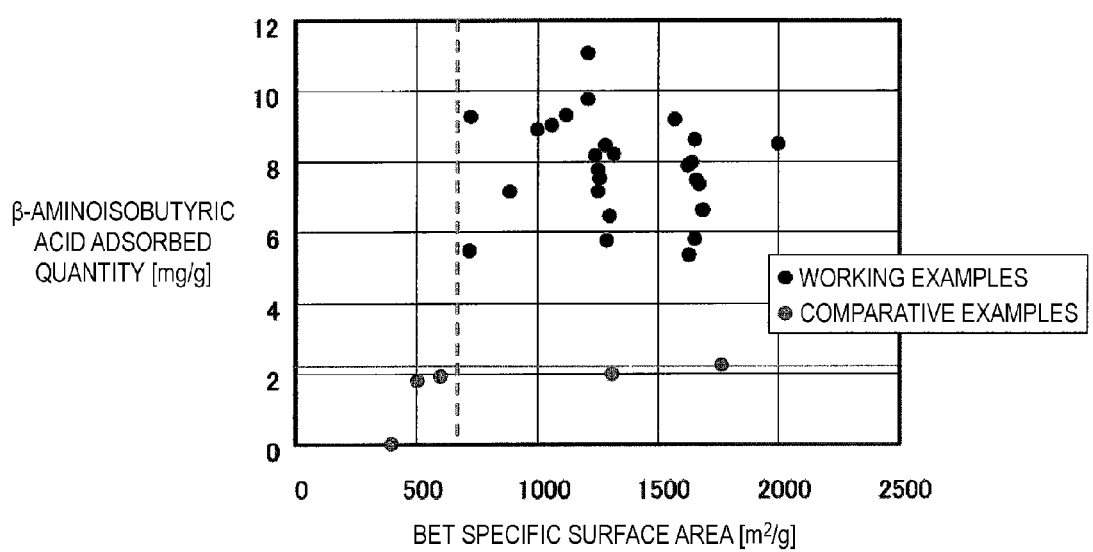
FIG. 3 is a graph showing the relationship between the BET specific surface area and -aminoisobutyric acid adsorbed quantity (24 hours) of orally administered adsorbents obtained in working examples and comparative examples.

The specific surface area of the spherical activated carbon can be determined by the BET method or the Langmuir method. The spherical activated carbon used for the orally administered adsorbent according to the present invention has a specific surface area determined by the BET method (sometimes abbreviated as "SSA" hereinafter) from 700 $m^2/g$ to 3000 $m^2/g$. When spherical activated carbon has SSA less than 700 $m^2/g$, toxin adsorption performance decreases, which is undesirable. The lower limit of SSA is more preferably not less than 1000 $m^2/g$. The upper limit of SSA is not particularly limited, but from the perspective of strength, SSA is preferably not greater than 3000 $m^2/g$. FIG. 3 illustrates the relationship between a BET specific surface area and -aminoisobutyric acid adsorbed quantity. As is understood from FIG. 3, when the specific surface area is less than 700 $m^2/g$, -aminoisobutyric acid adsorbed quantity decreases even if nitrogen content is not less than 0.5 wt %, which is undesirable.

(Total Acidic Group Content)

The spherical activated carbon used for the orally administered adsorbent according to the present invention is surface-unmodified spherical activated carbon. Here, surface-unmodified spherical activated carbon means spherical activated carbon having total acidic group content of less than 0.30 meq/g. Conversely, surface-modified spherical activated carbon means spherical activated carbon having total acidic group content of not less than 0.30 meq/g. As will be described later, surface-unmodified spherical activated carbon is a porous body obtained by performing activation treatment after heat-treating a carbon precursor, for example. It may be spherical activated carbon which has not subsequently undergone surface modification treatment by oxidation treatment and reduction treatment, or it may be spherical activated carbon obtained by performing heat treatment in a non-oxidative atmosphere after the aforementioned activation treatment. On the other hand, surface-modified spherical activated carbon is a porous body obtained by performing activation treatment after heat-treating a carbon precursor, and then further performing surface modification treatment by oxidation treatment and reduction treatment. It may exhibit appropriate degrees of interaction with acids and bases. The spherical activated carbon used in the orally administered adsorbent of the present invention is surface-unmodified spherical activated carbon, and therefore, the total acidic group content is less than 0.30 meq/g, preferably not greater than 0.25 meq/g, and more preferably not greater than 0.20 meq/g.

(Surface Modification)

Surface-modified spherical activated carbon can be obtained by performing oxidation treatment and reduction treatment on the surface-unmodified spherical activated carbon obtained using the above heat-fusible resin or heat-infusible resin as a carbon source. The oxidation treatment can be performed in an atmosphere containing from 0.1 vol % to 50 vol % oxygen, preferably from 1 vol % to 30 vol %, and particularly preferably from 3 vol % to 20 vol %, at a temperature from 300° C. to 800° C., and preferably from 320° C. to 600° C. The reduction treatment can be performed at a temperature from 800° C. to 1200° C. and preferably from 800° C. to 1000° C. in a non-oxidative gas atmosphere. In the specified oxygen-containing atmosphere, pure oxygen, nitrogen oxide, air, or the like may be used as the oxygen source. Furthermore, an atmosphere that is inert relative to carbon means nitrogen, argon, helium, or the like alone or in a mixture thereof. In this specification, surface-modified spherical activated carbon means a porous body obtained by performing the above oxidation treatment and reduction treatment on the above spherical activated carbon. By performing the oxidation treatment and reduction treatment, adsorption characteristics for toxins in the upper small intestine are improved due to the fact that an acidic point and a basic point are added in a good balance on the surface of the spherical activated carbon. For example, by performing oxidation treatment and reduction treatment on the above spherical activated carbon, specificity for toxins to be adsorbed can be improved.

However, the spherical activated carbon used for the orally administered adsorbent of the present invention may be used as-is in that state without performing subsequent steps of an oxidation step and a reduction step for carrying a functional group.

(Pore Volume)

The pore volume of pores having a pore diameter from 20 to 15,000 nm of the spherical activated carbon used in the orally administered adsorbent of the present invention is not particularly limited, but is preferably not greater than 1.00 mL/g, and more preferably not greater than 0.80 mL/g. The lower limit is not particularly limited, but is preferably not less than 0.01 mL/g.

The pore volume of pores having a pore diameter from 7.5 to 15,000 nm of the spherical activated carbon used in the orally administered adsorbent of the present invention is not particularly limited, but is preferably not greater than 1.00 mL/g, and more preferably not greater than 0.80 mL/g. The lower limit is not particularly limited, but is preferably not less than 0.01 mL/g.

The pore volume is measured using the mercury penetration method.

(Method for Producing Spherical Activated Carbon)

When a heat-fusible resin (for example, crosslinked vinyl resin) is used as the carbon source, the spheres formed of heat-fusible resin soften and deform into a non-spherical shape or fuse to each other when heat-treated. Therefore, softening can be reduced by performing oxidation treatment in an atmosphere containing oxygen from 150° C. to 400° C. as infusibility treatment prior to the above activation treatment. Specifically, by so-called infusibility treatment such as oxidation treatment, the heat-fusible resin can be used in production of spherical activated carbon after modifying the resin to a state in which melt oxidation can be avoided.

The crosslinked vinyl resin which is the heat-fusible resin softens and melts by the heat treatment in a non-oxidizing gas atmosphere and has a carbonization yield of less than 10%, but the crosslinked vinyl resin does not soften and melt by oxidation treatment in an atmosphere containing oxygen from 150° C. to 400° C. as infusibility treatment, and a spherical carbonaceous material can be obtained at a high carbonization yield of not less than 30%, and spherical activated carbon can be obtained by activation treatment on the resin in the same manner as the above heat-infusible resin.

In the preparation of the spherical activated carbon used for the orally administered adsorbent of the present invention, when heat-infusible resin (for example, ion exchange resin) is used as a carbon source, substantially the same operations as convention production methods using pitch can be employed. For example, spherical activated carbon can be obtained by first performing activation treatment under the flow of a gas that reacts with carbon (for example, steam or carbon dioxide gas) at a temperature from 700 to 1000° C. on spheres formed of heat-infusible resin. In a case where a large amount of pyrolysis gas is generated when the spheres of the heat-fusible resin after infusibility treatment or the heat-infusible resin are heat-treated, pyrolysis products can be removed in advance by appropriate pre-heat-treatment before the activation operation.

The above heat-infusible resin used as a starting material is a material that can be formed into spheres and, importantly, does not melt or soften and undergo shape deformation in heat treatment at a temperature not greater than 500° C.

For the above heat-infusible resin used as the starting material, it is desirable that carbonization yield by heat treatment is high. When carbonization yield is low, strength as spherical activated carbon will be low. Since unnecessary pores are otherwise formed, the bulk density of the spherical activated carbon decreases and the specific surface area per unit volume decreases, and therefore the administered volume increases, which leads to the problem that oral administration is difficult. Therefore, a higher carbonization yield of the heat-infusible resin is preferred, and the value of yield by heat treatment in a non-oxidizing gas atmosphere at 800° C. is preferably not less than 30 wt %, and more preferably not less than 35 wt %.

(Control of Physical Properties of Spherical Activated Carbon)

When preparing the spherical activated carbon according to the present invention using the above heat-fusible resin or heat-infusible resin, the physical properties of the spherical activated carbon (for example, average particle size, pore volume, specific surface area, and the like) can be controlled by various methods. For example, the average particle size of resin depends on the size of the droplets in the aqueous phase, and the size of the droplets can be controlled by the amount of suspending agent, the rotational frequency of stirring, the shape of the stirring blades, or the monomer ratio in the aqueous phase (ratio of amount of water to amount of monomer). For example, when the amount of suspending agent is increased, droplet size decreases, and when the rotational frequency of stirring is increased, droplet size decreases. Additionally, it is preferred that the amount of monomer in the aqueous phase be decreased from the perspective that not only coalescence of droplets can be controlled, but removal of heat of polymerization becomes easy as well. However, when the monomer ratio is too low, the amount of monomer per batch becomes small and the amount of synthetic resin obtained decreases, which is undesirable from the perspective of productivity.

Furthermore, when the pore diameter to be controlled is not less than 10 nm, the pore volume and specific surface area can be controlled primarily by the amount and type of porogen, and when the pore diameter to be controlled is not greater than 10 nm, the pore volume and specific surface area can be controlled by activation conditions using steam. For example, as the activation reaction, spherical activated carbon used for the orally administered adsorbent of the present invention can be obtained by activation treatment under the flow of a gas that reacts with carbon (for example, steam or carbon dioxide gas) at a temperature from 700 to 1000° C. The specific surface area can be controlled by the activation conditions. For example, the specific surface area can be increased by increasing the activation time, increasing the activation temperature, and increasing the concentration of the gas that reacts with carbon. Additionally, the fine structure as spherical activated carbon can be controlled by the type of resin, the type and amount of crosslinking agent, the infusibility conditions, and/or the activation temperature.

[2] Orally Administered Adsorbent for Therapy or Prophylaxis of Renal Disease or Hepatic Disease Because the spherical activated carbon used for the orally administered adsorbent of the present invention has excellent adsorbance of hepatic disease aggravating factors and toxins in renal diseases, the spherical activated carbon may be used as an orally administered adsorbent for therapy or prophylaxis of a renal disease or may be used as an orally administered adsorbent for therapy or prophylaxis of a hepatic disease. Examples of the renal disease include chronic renal failure, acute renal failure, chronic pyelonephritis, acute pyelonephritis, chronic nephritis, acute nephritic syndrome, acute progressive nephritic syndrome, chronic nephritic syndrome, nephrotic syndrome, nephrosclerosis, interstitial nephritis, tubulopathy, lipoid nephrosis, diabetic nephropathy, renovascular hypertension, and hypertension syndrome, or secondary renal diseases attendant to these primary diseases. Another example is pre-dialysis mild renal failure, and it may be used for condition improvement of mild renal failure before dialysis or condition improvement during dialysis (see "Clinical Nephrology," Asakura Publishing, N. Honda, K. Koiso, K. Kurogawa, 1990 edition, and "Nephrology," Igaku Shoin, T. Onomae, S. Fujimi, editors, 1981 edition).

Examples of the hepatic disease include fulminant hepatitis, chronic hepatitis, viral hepatitis, alcoholic hepatitis, hepatic fibrosis, cirrhosis, hepatic cancer, autoimmune hepatitis, drug-induced allergic hepatitis, primary biliary cirrhosis, tremor, encephalopathy, metabolic disorder, and functional disorder. Otherwise, it may also be used in therapy of illnesses caused by harmful substances present in the body, that is, mental illness and the like.

Therefore, when the orally administered adsorbent according to the present invention is used as a therapeutic medicine for a renal disease, the orally administered adsorbent contains the above spherical activated carbon as an active ingredient. When the orally administered adsorbent of the present invention is used as a therapeutic medicine for a renal disease or a therapeutic medicine for a hepatic disease, the dosage thereof is influenced by whether the subject of administration is a human or other animal, and by age, individual differences, disease condition, or the like. Therefore, depending on the case, a dosage outside the following range may be appropriate, but in general, the orally administered dosage in humans is from 1 to 20 g per day divided into three to four doses, and may be further adjusted according to symptoms. The administered form may be a powder, granules, tablet, sugar-coated pill, capsule, suspension, stick, individual package, emulsion, or the like. When ingested as a capsule, in addition to an ordinary gelatin capsule, an enteric-coated capsule may be used as necessary. When used as a tablet, it needs to be dissolved into microparticles in the body. Additionally, it may be used in the form of a complex blended with an electrolyte modifier such as alumigel or Kayexalate, which are other preparations.

Spherical activated carbon containing not less than 0.5 wt % nitrogen atoms, having a specific surface area determined by the BET method from 700 $m^2/g$ to 3000 $m^2/g$, and having an average particle size from 0.01 mm to 1 mm can be used as a therapeutic or prophylactic agent for a renal disease or a therapeutic or prophylactic agent for a hepatic disease in the form of a mixture with conventional known surface-modified spherical activated carbon or spherical activated carbon (that is, spherical activated carbon containing less than 0.5 wt % nitrogen atoms).

Alternatively, spherical activated carbon containing not less than 0.5 wt % nitrogen atoms, having a specific surface area determined by the BET method from 700 $m^2/g$ to 3000 $m^2/g$, and having an average particle size from 0.01 mm to 1 mm can be used as a therapeutic or prophylactic agent for a renal disease or a therapeutic or prophylactic agent for a hepatic disease by concomitant use with a conventional known surface-modified spherical activated carbon or spherical activated carbon (that is, spherical activated carbon containing less than 0.5 wt % nitrogen atoms).

[3] Method of Therapy of Renal Disease or Hepatic Disease

The spherical activated carbon used in the orally administered adsorbent according to the present invention can be used in a method of prophylaxis or therapy of a renal disease or a hepatic disease. Therefore, the method of therapy of a renal disease or a hepatic disease of the present invention is characterized in that the above orally administered adsorbent containing spherical activated carbon is administered in an effective dose to a renal disease or hepatic disease therapy subject.

The administration route, dosage, administration interval, and the like of the above spherical activated carbon may be determined as appropriate in accordance with the type of illness, the age, gender, and body weight of the patient, the degree of symptoms, the dosing method, and the like.

[4] Spherical Activated Carbon for Use in Method of Therapy of Renal Disease or Hepatic Disease The spherical activated carbon used in the orally administered adsorbent according to the present invention can be used in a method of prophylaxis or therapy of a renal disease or a hepatic disease. Therefore, the spherical activated carbon of the present invention is for use in a method of prophylaxis or therapy of a renal disease or a hepatic disease.

The amount and the like of the above spherical activated carbon used in prophylaxis or therapy may be determined as appropriate in accordance with the type of illness, the age, gender, and body weight of the patient, the degree of symptoms, the dosing method, and the like.

[5] Use of Spherical Activated Carbon for Production of Therapeutic Medicine for Renal Disease or Hepatic Disease The spherical activated carbon used in the orally administered adsorbent according to the present invention can be used for producing a prophylactic or therapeutic medicine for a renal disease or a hepatic disease. Therefore, use of the present invention is use of spherical activated carbon for producing a medicine for prophylaxis or therapy of a renal disease or a hepatic disease.

The contained amount and the like of the above spherical activated carbon in the prophylactic or therapeutic medicine may be determined as appropriate in accordance with the type of illness, the age, gender, and body weight of the patient, the degree of symptoms, the dosing method, and the like.

[6] Use of Spherical Activated Carbon for Therapy of Renal Disease or Hepatic Disease The spherical activated carbon used in the orally administered adsorbent according to the present invention can be used for therapy of a renal disease or a hepatic disease. Therefore, use of the present invention is use of spherical activated carbon for prophylaxis or therapy of a renal disease or a hepatic disease.

The amount and the like of the above spherical activated carbon used in prophylaxis or therapy may be determined as appropriate in accordance with the type of illness, the age, gender, and body weight of the patient, the degree of symptoms, the dosing method, and the like.

EXAMPLES

The present invention will be described in detail hereinafter using working examples, but these working examples do not limit the scope of the present invention.

Working Example 1

4500 g of deionized water, 0.9 g of sodium nitrite, and 6.8 g of Metalose 60SH-15 (Shin-Etsu Chemical Co., Ltd.) were put in a 10-L polymerization reactor. To this were added 376 g of styrene, 1049 g of divinylbenzene (57% divinylbenzene and 43% ethylvinylbenzene), 75 g of acrylonitrile, 8.7 g of 2,2'-azobis(2,4-dimethylvaleronitrile), and 525 g of hexane as a porogen, and the interior of the system was then replaced with nitrogen gas. This two-phase system was heated to 55° C. while stirring at 180 rpm, and then held in that state for 20 hours. The obtained resin was washed with water and filtered, and then dried for 16 hours at 180° C. under nitrogen flow, to produce a spherical porous synthetic resin having an average particle size of 197 μm.

The obtained spherical porous synthetic resin was put in a reaction tube with a grating, and infusibility treatment was performed in a vertical tube furnace. As the infusibility treatment, dry air was made to flow from bottom to top of the reaction tube, and after heating to 180° C., the temperature was raised from 180° C. to 240° C. in 3 hours, and then held at 240° C. for 1 hour. The temperature was then raised from 240° C. to 250° C. in 30 minutes and held at 250° C. in 2 hours, and then raised from 250° C. to 260° C. in 30 minutes and held at 260° C. for 3 hours. The temperature was then raised from 260° C. to 300° C. for 2 hours and held at 300° C. for 1 hour, and spherical porous oxidized resin was thereby obtained. The obtained spherical porous oxidized resin was heated in a nitrogen atmosphere at 850° C., and then, using a fluidized bed, activation treatment was performed in a nitrogen atmosphere containing steam at 850° C. until the BET specific surface area reached 1290 m$^2$/g, and spherical activated carbon was thereby obtained. The characteristics of the obtained spherical activated carbon are shown in Table 1.

Working Example 2

Spherical porous synthetic resin was prepared by repeating the resin preparation operations of Working Example 1 except that 301 g of styrene and 150 g of acrylonitrile were used. The average particle size of the obtained spherical porous synthetic resin was 193 μm.

Additionally, spherical activated carbon was prepared by repeating the infusibility treatment and activation treatment of Working Example 1 except that the above spherical porous synthetic resin was used, and activation treatment was performed until the BET specific surface area reached 1630 m$^2$/g. The characteristics of the obtained spherical activated carbon are shown in Table 1.

Working Example 3

Spherical porous synthetic resin was prepared by repeating the resin preparation operations of Working Example 1 except that 151 g of styrene and 300 g of acrylonitrile were used and the stirring rotational frequency of the two-phase system was 168 rpm. The average particle size of the obtained spherical porous synthetic resin was 152 μm. Additionally, spherical activated carbon was prepared by repeating the infusibility treatment and activation treatment of Working Example 1 except that the above spherical porous synthetic resin was used, and activation treatment was performed until the BET specific surface area reached 1620 m$^2$/g. The characteristics of the obtained spherical activated carbon are shown in Table 1.

Working Example 4

4500 g of deionized water, 6.0 g of sodium nitrite, and 6.8 g of Metalose 60SH-15 (Shin-Etsu Chemical Co., Ltd.) were put in a 10-L polymerization reactor. To this were added 582 g of styrene, 393 g of divinylbenzene (57% divinylbenzene and 43% ethylvinylbenzene), 525 g of acrylonitrile, 8.7 g of 2,2'-azobis(2,4-dimethylvaleronitrile), and 375 g of hexane as a porogen, and the interior of the system was then replaced with nitrogen gas. This two-phase system was heated to 55° C. while stirring at 150 rpm, and then held in that state for 20 hours. The obtained resin was washed with water and filtered, and then dried for 16 hours at 180° C. under nitrogen flow. The average particle size of the obtained spherical porous synthetic resin was 171 μm.

The obtained spherical porous synthetic resin was put in a reaction tube with a grating, and infusibility treatment was performed in a vertical tube furnace. As the infusibility treatment, dry air was made to flow from bottom to top of the reaction tube, and after heating to 180° C., the temperature was raised from 180° C. to 240° C. in 3 hours, and then held at 240° C. for 1 hour. The temperature was then raised from 240° C. to 260° C. in 1 hour and held at 260° C. for 5 hours, and then raised from 260° C. to 300° C. in 2 hours and held at 300° C. for 1 hour, and spherical porous oxidized resin was thereby obtained. The obtained spherical porous oxidized resin was heated in a nitrogen atmosphere at 850° C., and then, using a fluidized bed, activation treatment was performed in a nitrogen atmosphere containing steam at 850° C. until the BET specific surface area reached 1670 $m^2/g$, and spherical activated carbon was thereby obtained. The characteristics of the obtained spherical activated carbon are shown in Table 1.

Working Example 5

Spherical porous synthetic resin was prepared by repeating the resin preparation operations of Working Example 4 except that 432 g of styrene and 675 g of acrylonitrile were used and the stirring rotational frequency of the two-phase system was 147 rpm. The average particle size of the obtained spherical porous synthetic resin was 190 μm. The obtained spherical porous synthetic resin was put in a reaction tube with a grating, and infusibility treatment was performed in a vertical tube furnace. As the infusibility treatment, dry air was made to flow from bottom to top of the reaction tube, and after heating to 180° C., the temperature was raised from 180° C. to 240° C. in 3 hours, and then held at 240° C. for 1 hour. The temperature was then raised from 240° C. to 260° C. in 1 hour and held at 260° C. for 5 hours, and spherical porous oxidized resin was thereby obtained. The obtained spherical porous oxidized resin was heated in a nitrogen atmosphere at 850° C., and then, using a fluidized bed, activation treatment was performed in a nitrogen atmosphere containing steam at 850° C. until the BET specific surface area reached 1640 $m^2/g$, and spherical activated carbon was thereby obtained. The characteristics of the obtained spherical activated carbon are shown in Table 1.

Working Example 6

Spherical porous synthetic resin was prepared by repeating the resin preparation operations of Working Example 5 except that 207 g of styrene, 900 g of acrylonitrile, and 450 g of hexane were used and the stirring rotational frequency of the two-phase system was 135 rpm. The average particle size of the obtained spherical porous synthetic resin was 172 μm.

Additionally, spherical activated carbon was prepared by repeating the infusibility treatment and activation treatment of Working Example 5 except that the above spherical porous synthetic resin was used, and activation treatment was performed until the BET specific surface area reached 1690 $m^2/g$. The characteristics of the obtained spherical activated carbon are shown in Table 1.

Working Example 7

4800 g of deionized water, 1.0 g of sodium nitrite, and 7.2 g of Metalose 60SH-15 (Shin-Etsu Chemical Co., Ltd.) were put in a 10-L polymerization reactor. To this were added 280 g of divinylbenzene (57% divinylbenzene and 43% ethylvinylbenzene), 1320 g of acrylonitrile, and 18.6 g of 2,2'-azobis(2,4-dimethylvaleronitrile), and the interior of the system was then replaced with nitrogen gas. This two-phase system was heated to 55° C. while stirring at 150 rpm, and then held in that state for 20 hours. The obtained resin was washed with water and filtered, and then dried for 16 hours at 180° C. under nitrogen flow, to produce spherical porous synthetic resin having an average particle size of 221 μm. The obtained spherical porous synthetic resin was put in a reaction tube with a grating, and infusibility treatment was performed in a vertical tube furnace. As the infusibility treatment, dry air was made to flow from bottom to top of the reaction tube, and after heating to 190° C., the temperature was raised from 190° C. to 290° C. in 2 hours 30 minutes, and then held at 290° C. for 2 hours, and spherical porous oxidized resin was thereby obtained. This spherical porous oxidized resin was heated in a nitrogen atmosphere at 850° C., and then, using a fluidized bed, activation treatment was performed in a nitrogen atmosphere containing steam at 850° C. until the BET specific surface area reached 1120 $m^2/g$, and spherical activated carbon was thereby obtained. The characteristics of the obtained spherical activated carbon are shown in Table 1.

Working Example 8

Synthetic resin was prepared by repeating the resin preparation operations of Working Example 6 except that 1500 g of acrylonitrile, 0 g of styrene, and 0 g of divinylbenzene (57% divinylbenzene and 43% ethylvinylbenzene) were used and the stirring rotational frequency of the two-phase system was 140 rpm. Using a sieve with 212-μm openings, resin particles larger than the openings were removed from the obtained synthetic resin, and spherical porous synthetic resin having an average particle size of 166 μm was obtained.

The obtained spherical porous synthetic resin was put in a reaction tube with a grating, and infusibility treatment was performed in a vertical tube furnace. As the infusibility treatment, dry air was made to flow from bottom to top of the reaction tube, and after heating to 180° C., the temperature was raised from 180° C. to 240° C. in 3 hours, and then held at 240° C. for 1 hour. The temperature was then raised from 240° C. to 260° C. in 1 hour and held at 260° C. for 4 hours, and spherical porous oxidized resin was thereby obtained. The spherical porous oxidized resin was heated in a nitrogen atmosphere at 850° C., and then, using a fluidized bed, activation treatment was performed in a nitrogen atmosphere containing steam at 850° C. until the BET specific surface area reached 1210 $m^2/g$, and spherical activated carbon was thereby obtained. The characteristics of the obtained spherical activated carbon are shown in Table 1.

Working Example 9

Spherical activated carbon was prepared by repeating the operations of Working Example 8 except that activation treatment was performed until the BET specific surface area reached 1000 $m^2/g$. The characteristics of the obtained spherical activated carbon are shown in Table 1.

Working Example 10

Weakly basic anion exchange resin (brand name "Diaion WA30," lot No. 1L102; Mitsubishi Chemical Corp.) was put in a reaction tube with a grating, and infusibility treatment was performed in a vertical tube furnace. As the infusibility condition, dry air was made to flow from bottom to top of the reaction tube, and after heating to 180° C., the temperature was raised from 180° C. to 300° C. in 3 hours, and then held at 300° C. for 1 hour. The resultant was heated in a nitrogen atmosphere at 850° C., and then, using a fluidized bed, activation treatment was performed in a nitrogen atmosphere containing steam at 850° C. until BET specific surface area reached 730 m²/g, and spherical activated carbon was thereby obtained. The characteristics of the obtained spherical activated carbon are shown in Table 1.

Working Example 11

Spherical activated carbon was prepared by repeating the operations of Working Example 10 except that weakly basic anion exchange resin (brand name "Diaion WA21J," lot No. 9H182; Mitsubishi Chemical Corp.) was used, and activation treatment was performed until the BET specific surface area reached 1570 m²/g. The characteristics of the obtained spherical activated carbon are shown in Table 1.

Working Example 12

Spherical activated carbon was prepared by repeating the operations of Working Example 10 except that amphoteric ion exchange resin (brand name "Diaion AMP03," lot No. 1B102; Mitsubishi Chemical Corp.) was used, and activation treatment was performed until the BET specific surface area reached 1210 m²/g. The characteristics of the obtained spherical activated carbon are shown in Table 1.

Working Example 13

Spherical activated carbon was prepared by repeating the operations of Working Example 3 except that activation treatment was performed until the BET specific surface area reached 1240 m²/g. The characteristics of the obtained spherical activated carbon are shown in Table 1.

Working Example 14

Spherical activated carbon was prepared by repeating the operations of Working Example 4 except that treatment was performed until the BET specific surface area reached 720 m²/g. The characteristics of the obtained spherical activated carbon are shown in Table 1.

Working Example 15

Spherical activated carbon was prepared by repeating the operations of Working Example 4 except that treatment was performed until the BET specific surface area reached 890 m²/g. The characteristics of the obtained spherical activated carbon are shown in Table 1.

Working Example 16

Spherical activated carbon was prepared by repeating the operations of Working Example 4 except that treatment was performed until the BET specific surface area reached 1060 m²/g. The characteristics of the obtained spherical activated carbon are shown in Table 1.

Working Example 17

Spherical activated carbon was prepared by repeating the operations of Working Example 4 except that treatment was performed until the BET specific surface area reached 1280 m²/g. The characteristics of the obtained spherical activated carbon are shown in Table 1.

Working Example 18

Spherical activated carbon was prepared by repeating the operations of Working Example 4 except that treatment was performed until the BET specific surface area reached 2000 m²/g. The characteristics of the obtained spherical activated carbon are shown in Table 1.

Working Example 19

Spherical porous synthetic resin was prepared by repeating the resin preparation operations of Working Example 5 except that the stirring rotational frequency of the two-phase system was 120 rpm. The average particle size of the obtained spherical porous synthetic resin was 246 μm.

The obtained spherical porous synthetic resin was put in a reaction tube with a grating, and infusibility treatment was performed in a vertical tube furnace. As the infusibility treatment, dry air was made to flow from bottom to top of the reaction tube, and after heating to 180° C., the temperature was raised from 180° C. to 240° C. in 3 hours, and then held at 240° C. for 1 hour. The temperature was then raised from 240° C. to 260° C. in 1 hour and held at 260° C. for 5 hours, and then raised from 260° C. to 300° C. in 2 hours and held at 300° C. for 1 hour, and spherical porous oxidized resin was thereby obtained. The obtained spherical porous oxidized resin was heated in a nitrogen atmosphere at 850° C., and then, using a fluidized bed, activation treatment was performed in a nitrogen atmosphere containing steam at 850° C. until the BET specific surface area reached 1320 m²/g, and spherical activated carbon was thereby obtained. The characteristics of the obtained spherical activated carbon are shown in Table 1.

Working Example 20

Spherical porous synthetic resin was prepared by repeating the resin preparation operations of Working Example 4 except that 13.5 g of methylcellulose (60SH-15) was used and the stirring rotational frequency of the two-phase system was 186 rpm. The average particle size of the obtained spherical porous synthetic resin was 135 μm. Additionally, spherical activated carbon was prepared by repeating the infusibility treatment and activation treatment of Working Example 1 except that the above spherical porous synthetic resin was used, and activation treatment was performed until the BET specific surface area reached 1650 m²/g. The characteristics of the obtained spherical activated carbon are shown in Table 1.

Working Example 21

Spherical porous synthetic resin was prepared by repeating the resin preparation operations of Working Example 4 except that the stirring rotational frequency of the two-phase system was 120 rpm. The average particle size of the obtained spherical porous synthetic resin was 249 μm.

Spherical activated carbon was prepared by repeating the operations of infusibility treatment and activation treatment of Working Example 4 except that the above spherical porous synthetic resin was used, the heating temperature was 850° C. instead of 690° C., the activation temperature was 850° C. instead of 900° C., and activation treatment was

Working Example 22

Spherical porous synthetic resin was prepared by repeating the resin preparation operations of Working Example 4 except that 6.8 g of methylcellulose (SM-400) was used instead of 6.8 g of methylcellulose (60SH-15) and the stirring rotational frequency of the two-phase system was 110 rpm. The average particle size of the obtained spherical porous synthetic resin was 367 μm.

The obtained spherical porous synthetic resin was put in a reaction tube with a grating, and infusibility treatment was performed in a vertical tube furnace. As the infusibility treatment, dry air was made to flow from bottom to top of the reaction tube, and after heating to 180° C., the temperature was raised from 180° C. to 240° C. in 3 hours, and then held at 240° C. for 1 hour. The temperature was then raised from 240° C. to 260° C. in 1 hour and held at 260° C. for 5 hours 40 minutes, and then raised from 260° C. to 300° C. in 2 hours and held at 300° C. for 1 hour 30 minutes, and spherical porous oxidized resin was thereby obtained. The obtained spherical porous oxidized resin was heated in a nitrogen atmosphere at 850° C., and then, using a fluidized bed, activation treatment was performed in a nitrogen atmosphere containing steam at 850° C. until the BET specific surface area reached 1650 $m^2/g$, and spherical activated carbon was thereby obtained. The characteristics of the obtained spherical activated carbon are shown in Table 1.

Working Example 23

Spherical porous synthetic resin was prepared by repeating the resin preparation operations of Working Example 4 except that 3.4 g of Metolose SM-100 (Shin-Etsu Chemical Co., Ltd.) was used instead of 6.8 g of methylcellulose (60SH-15) and the stirring rotational frequency of the two-phase system was 75 rpm. The average particle size of the obtained spherical porous synthetic resin was 735 μm.

The obtained spherical porous synthetic resin was put in a reaction tube with a grating, and infusibility treatment was performed in a vertical tube furnace. As the infusibility treatment, dry air was made to flow from bottom to top of the reaction tube, and after heating to 180° C., the temperature was raised from 180° C. to 240° C. in 3 hours, and then held at 240° C. for 1 hour. The temperature was then raised from 240° C. to 260° C. in 1 hour and held at 260° C. for 5 hours 40 minutes, and then raised from 260° C. to 300° C. in 2 hours and held at 300° C. for 1 hour, and spherical porous oxidized resin was thereby obtained. The obtained spherical porous oxidized resin was heated in a nitrogen atmosphere at 850° C., and then, using a fluidized bed, activation treatment was performed in a nitrogen atmosphere containing steam at 850° C. until the BET specific surface area reached 1680 $m^2/g$, and spherical activated carbon was thereby obtained. The characteristics of the obtained spherical activated carbon are shown in Table 1.

Working Example 24

Spherical activated carbon was prepared by repeating the operations of Working Example 20 except that activation treatment was performed until the BET specific surface area reached 1250 $m^2/g$. The characteristics of the obtained spherical activated carbon are shown in Table 1.

Working Example 25

Spherical activated carbon was prepared by repeating the operations of Working Example 21 except that activation treatment was performed until the BET specific surface area reached 1260 $m^2/g$. The characteristics of the obtained spherical activated carbon are shown in Table 1.

Working Example 26

Spherical activated carbon was prepared by repeating the operations of Working Example 22 except that activation treatment was performed until the BET specific surface area reached 1250 $m^2/g$. The characteristics of the obtained spherical activated carbon are shown in Table 1.

Working Example 27

Spherical activated carbon was prepared by repeating the operations of Working Example 23 except that activation treatment was performed until the BET specific surface area reached 1300 $m^2/g$. The characteristics of the obtained spherical activated carbon are shown in Table 1.

Comparative Example 1

4800 g of deionized water, 1.0 g of sodium nitrite, and 7.2 g of Metalose 60SH-15 (Shin-Etsu Chemical Co., Ltd.) were put in a 10-L polymerization reactor. To this were added 481 g of styrene, 1119 g of divinylbenzene (57% divinylbenzene and 43% ethylvinylbenzene), 9.3 g of 2,2'-azobis(2,4-dimethylvaleronitrile), and 560 g of hexane as a porogen, and the interior of the system was then replaced with nitrogen gas. This two-phase system was heated to 55° C. while stirring at 140 rpm, and then held in that state for 20 hours. The obtained resin was washed with water and filtered, and then hexane was removed from the resin by evaporation by vacuum-drying. The resulting resin was vacuum-dried for 12 hours at 90° C., to obtain spherical porous synthetic resin having an average particle size of 246 μm.

The obtained spherical porous synthetic resin was put in a reaction tube with a grating, and infusibility treatment was performed in a vertical tube furnace. As the infusibility treatment, dry air was made to flow from bottom to top of the reaction tube, and after heating to 190° C., the temperature was raised from 190° C. to 290° C. at 10° C./minute, and spherical porous oxidized resin was thereby obtained. The obtained spherical porous oxidized resin was heated in a nitrogen atmosphere at 850° C., and then, using a fluidized bed, activation treatment was performed in a nitrogen atmosphere containing steam at 850° C. until the BET specific surface area reached 1780 $m^2/g$, and spherical activated carbon was thereby obtained. The characteristics of the obtained spherical activated carbon are shown in Table 1.

Comparative Example 2

Spherical activated carbon was prepared by repeating the operations of Comparative Example 1 except that activation treatment was performed until the BET specific surface area reached 1300 $m^2/g$. The characteristics of the obtained spherical activated carbon are shown in Table 1.

Comparative Example 3

Spherical activated carbon was prepared by repeating the operations of Working Example 3 except that activation treatment was not performed. The characteristics of the obtained spherical activated carbon are shown in Table 1.

Comparative Example 4

Spherical activated carbon was prepared by repeating the operations of Working Example 4 except that activation treatment was not performed. The characteristics of the obtained spherical activated carbon are shown in Table 1.

Comparative Example 5

Spherical activated carbon was prepared by repeating the operations of Working Example 4 except that treatment was performed until the BET specific surface area reached 600 m²/g. The characteristics of the obtained spherical activated carbon are shown in Table 1.

(Method for Evaluating Oral Adsorbent)

The various characteristics shown in Table 1 below were measured by the following methods.

(1) Average Particle Size (Dv50)

The particle diameter at a cumulative particle size percentage of 50% on a volume standard cumulative particle size distribution curve created using a laser diffraction-style particle size distribution analyzer (SALAD-3000S; Shimadzu Corp.) was used as the average particle size (Dv50).

(2) Specific Surface Area (Specific Surface Area Calculation Method by BET Method)

The gas adsorption quantity of a spherical activated carbon sample can be measured using a specific surface area analyzer that uses the gas adsorption method (for example, ASAP2010 or ASAP2020; Micromeritics Corp.), and a specific surface area can be calculated using the formula below. Specifically, a sample tube is packed with the spherical activated carbon sample, and after vacuum-drying at 350° C., post-drying sample weight is measured. Then, the sample tube is cooled to −196° C. and nitrogen is introduced into the sample tube to adsorb nitrogen on the spherical activated carbon sample, and the relationship between nitrogen partial pressure and adsorbed quantity (adsorption isotherm) is measured.

A BET plot is created, with the relative pressure of nitrogen taken as p and the adsorbed quantity at that time taken as v (cm³/g STP). Specifically, the range of p from 0.05 to 0.20 is plotted with p/(v(1−p)) on the vertical axis and p on the horizontal axis, and the specific surface area S (units: m²/g) is determined by the following formula from the slope b (units: g/cm³) and intercept c (units: g/cm³) at that time.

$$S = \frac{MA \times (6.02 \times 10^{23})}{22414 \times 10^{18} \times (b+c)} \quad \text{[Formula 1]}$$

MA is the cross-sectional area of a nitrogen molecule, and a value of 0.162 nm² was used here.

(3) Specific Surface Area (Specific Surface Area Calculation Method by Langmuir Equation)

The gas adsorption quantity of a spherical activated carbon sample can be measured using a specific surface area analyzer that uses the gas adsorption method (for example, ASAP2010 or ASAP2020; Micromeritics Corp.), and a specific surface area can be calculated using the Langmuir equation. Specifically, a sample tube is packed with the spherical activated carbon sample, and after vacuum-drying at 350° C., post-drying sample weight is measured. Then, the sample tube is cooled to −196° C. and nitrogen is introduced into the sample tube to adsorb nitrogen on the spherical activated carbon sample, and the relationship between nitrogen partial pressure and adsorbed quantity (adsorption isotherm) is measured.

A Langmuir plot is created, with the relative pressure of nitrogen taken as p and the adsorbed quantity at that time taken as v (cm³/g STP). Specifically, the range of p from 0.05 to 0.20 is plotted with p/v on the vertical axis and p on the horizontal axis, and the specific surface area S (units: m²/g) is determined by the following formula when the slope at that time is taken as b (units: g/cm³).

$$S = \frac{MA \times (6.02 \times 10^{23})}{22414 \times 10^{18} \times b}$$

MA is the cross-sectional area of a nitrogen molecule, and a value of 0.162 nm² was used here.

(4) Elemental Analysis (Content of Carbon, Hydrogen, Carbon, and Oxygen Atoms)

The organic elemental composition of a spherical activated carbon sample can be determined using an organic elemental analyzer (2400 Series II CHNS/O; PerkinElmer, Inc.). Specifically, 1.7 mg of sample was precisely weighed out and enclosed in a tin capsule. The sample was completely combusted in a 975° C. combustion tube mounted on an organic elemental analyzer, and by measuring the amounts of carbon dioxide, water, and nitrogen dioxide in the produced gas, the contents (wt %) of carbon, hydrogen, and nitrogen atoms in the sample were determined. Furthermore, the oxygen content (wt %) was calculated by subtracting the total content (wt %) of carbon, hydrogen, and nitrogen atoms in the sample from 100 wt %.

(5) Pore Volume by Mercury Penetration Method

Pore volume can be measured using a mercury porosimeter (for example, Autopore 9200; Micromeritics Corp.). The spherical activated carbon sample is put in a sample container, and degassed for 30 minutes under pressure not greater than 2.67 Pa. Then, mercury is introduced into the sample container, pressure is gradually increased, and the mercury penetrates into the pores of the spherical activated carbon (maximum pressure: 414 MPa). From the relationship between pressure and mercury penetration quantity at this time, the pore volume distribution of the spherical activated carbon sample is measured using the calculation formulas below.

Specifically, the volume of mercury that penetrates the spherical activated carbon sample is measured from a pressure equivalent to pore diameter 21 μm (0.06 MPa) to the maximum pressure (414 MPa, equivalent to pore diameter 3 nm). In the calculation of pore diameter, when mercury penetrates into the pores of a cylinder having a diameter (D) at a pressure (P), and the surface tension of mercury is taken as "□" and the contact angle between mercury and the pore wall is taken as "□" the following equation $$-\Box D \Box \cos \Box = \Box (D/2)^2 P$$

holds true based on the equilibrium of surface tension and the pressure that acts on the pore cross-section. Therefore, $$D = (-4\Box \cos \Box)/P$$

In this specification, the surface tension of mercury is taken as 484 dyne/cm and the contact angle between mercury and carbon is taken as 130 degrees. When the pressure P is expressed in MPa and the pore diameter D is expressed in μm, the relationship between pressure P and pore diameter D is determined using the following formula:

$$D = 1.24/P$$

For example, the pore volume in the range of pore diameter from 20 to 15,000 nm is equivalent to the volume of mercury that penetrates at mercury penetration pressure from 0.124 MPa to 165 MPa. Also, the pore volume in the range of pore diameter from 7.5 to 15,000 nm is equivalent to the volume of mercury that penetrates at mercury penetration pressure from 0.083 MPa to 165 MPa.

Furthermore, because the spherical activated carbon used for the orally administered adsorbent of the present invention has an extremely small particle size, the spaces between sample particles packed in the sample container are also small. Therefore, in the operation of pore volume measurement by the above mercury penetration method, there is a stage at which the mercury penetrates those interparticle spaces, and at that penetration stage, it behaves as if there are pores having a diameter from 8000 to 15,000 nm. It can be confirmed by observation using, for example, an electron microscope that no pores having a diameter from 8000 to 15,000 nm are present in the spherical activated carbon used for the orally administered adsorbent of the present invention. Therefore, in this specification, "pore volume in the range of pore diameter from 20 to 15,000 nm" and "pore volume in the range of pore diameter from 7.5 to 15,000 nm" also include the amount of mercury that penetrates the interparticle spaces.

(6) Total Acidic Group Content 1 g of spherical activated carbon sample was added to 50 mL of 0.05 N NaOH solution, and this was shaken in a figure-eight with an amplitude of 3 cm at 76 cycles/minute at 37° C. for 48 hours using a figure-eight shaker (Triple Shaker NR-80; Taitec Corp.). The spherical activated carbon sample was then filtered out, and the consumed amount of NaOH determined by neutralization titration was taken as the total acidic group content.

(7) DL- -Aminoisobutyric Acid Adsorbed Quantity Test

After the spherical activated carbon sample was dried, 0.100 g of the dried sample was precisely weighed out and added to a 50-mL screw-cap vial containing 50 mL precisely weighted out of 1000 mL of liquid (stock solution) obtained by precisely weighing 0.100 g of -aminoisobutyric acid in advance, adding phosphate buffer solution of pH 7.4 to the -aminoisobutyric acid and dissolving the -aminoisobutyric acid. The resulting solution was shaken for 3 hours or 24 hours at 37° C. at 10 rpm using a mix rotor (Mix Rotor Variable VMR-5R; Asone Corp.). The contents in the screw-cap vial which had undergone shaking were suction-filtered using a membrane filter with 0.80 μm pores to produce a sample solution.

Meanwhile, as standard samples, 50 mL each of the stock solution, a mixture of the stock solution and phosphate buffer solution of pH 7.4 mixed in a ratio of 1:1, and phosphate buffer solution of pH 7.4 was put in a 50-mL screw-top vial, and was shaken for 3 hours or 24 hours at 37° C. at 30 rpm using a mix rotor. The contents in the screw-cap vials which had undergone shaking were suction-filtered using a membrane filter with 0.80 μm pores to produce standard sample solutions.

For the sample solution and standard sample solutions, the organic carbon quantity was measured using a total organic carbon analyzer (TOC-L CPN; Shimadzu Corp.). A DL- -aminoisobutyric acid calibration curve was created from the stoichiometric concentration of DL- -aminoisobutyric acid versus organic carbon quantity in the standard sample solutions, and the DL- -aminoisobutyric acid concentration Ct (mg/L) of the sample solution was determined using this curve.

The quantity of DL- -aminoisobutyric acid adsorbed by the spherical activated carbon was determined using the following formula.

DL- -aminoisobutyric acid adsorbed quantity
$(mg/g) = (C0 - Ct) \times V/Mt$

Here, C0 is the DL- -aminoisobutyric acid concentration (mg/L) of the stock solution, Ct is the DL- -aminoisobutyric acid concentration (mg/L) of the sample solution, V is the initial volume of the sample solution (L), and Mt is the amount of spherical activated carbon (g).

The results are shown in Table 1.

TABLE 1

| | Average particle size [μm] | Specific surface area | | Elemental analysis | | | |
|---|---|---|---|---|---|---|---|
| | | Langmuir [m²/g] | BET [m²/g] | Carbon [wt %] | Hydrogen [wt %] | Nitrogen [wt %] | Oxygen [wt %] |
| Working Example 1 | 116 | 1758 | 1290 | 95.7 | 0.6 | 0.5 | 3.2 |
| Working Example 2 | 110 | 2247 | 1630 | 96.2 | 0.6 | 0.7 | 2.6 |
| Working Example 3 | 119 | 2202 | 1620 | 95.8 | 0.7 | 1.1 | 2.4 |
| Working Example 4 | 102 | 2293 | 1670 | 95.8 | 0.5 | 1.4 | 2.3 |
| Working Example 5 | 103 | 2242 | 1640 | 94.1 | 0.8 | 1.7 | 3.4 |
| Working Example 6 | 92 | 2314 | 1690 | 93.6 | 0.8 | 1.9 | 3.8 |
| Working Example 7 | 99 | 1520 | 1120 | 88.2 | 1.0 | 4.4 | 6.4 |
| Working Example 8 | 95 | 1631 | 1210 | 88.9 | 1.3 | 4.8 | 5.0 |
| Working Example 9 | 107 | 1362 | 1000 | 89.5 | 1.0 | 6.6 | 2.9 |
| Working Example 10 | 416 | 973 | 730 | 95.6 | 0.6 | 1.5 | 2.2 |
| Working Example 11 | 347 | 2147 | 1570 | 95.0 | 0.5 | 1.6 | 2.9 |
| Working Example 12 | 118 | 1662 | 1210 | 94.5 | 0.6 | 1.5 | 3.5 |
| Working Example 13 | 122 | 1705 | 1240 | 94.1 | 0.7 | 1.4 | 3.8 |
| Working Example 14 | 118 | 965 | 720 | 91.2 | 0.9 | 3.5 | 4.5 |
| Working Example 15 | 112 | 1172 | 890 | 91.8 | 0.7 | 3.2 | 4.3 |
| Working Example 16 | 102 | 1444 | 1060 | 93.4 | 0.6 | 2.5 | 3.4 |
| Working Example 17 | 107 | 1731 | 1280 | 95.1 | 0.3 | 1.8 | 2.8 |
| Working Example 18 | 90 | 2749 | 2000 | 94.7 | 0.6 | 1.3 | 3.4 |
| Working Example 19 | 140 | 1820 | 1320 | 92.9 | 0.8 | 2.5 | 3.9 |
| Working Example 20 | 81 | 2255 | 1650 | 95.1 | 0.5 | 1.5 | 2.9 |
| Working Example 21 | 135 | 2272 | 1660 | 93.0 | 0.5 | 1.6 | 4.8 |
| Working Example 22 | 208 | 2249 | 1650 | 94.3 | 0.7 | 1.7 | 3.3 |
| Working Example 23 | 449 | 2309 | 1680 | 94.5 | 0.6 | 1.9 | 3.0 |

TABLE 1-continued

| | | | | | | | |
|---|---|---|---|---|---|---|---|
| Working Example 24 | 88 | 1625 | 1250 | 93.6 | 0.7 | 2.1 | 3.6 |
| Working Example 25 | 147 | 1730 | 1260 | 92.4 | 0.9 | 2.1 | 4.5 |
| Working Example 26 | 217 | 1714 | 1250 | 94.3 | 0.7 | 2.2 | 2.9 |
| Working Example 27 | 417 | 1782 | 1300 | 93.6 | 0.7 | 2.6 | 3.1 |
| Comparative Example 1 | 127 | 2310 | 1780 | 94.7 | 0.2 | 0.0 | 5.2 |
| Comparative Example 2 | 127 | 1640 | 1300 | 93.4 | 0.3 | 0.0 | 6.4 |
| Comparative Example 3 | 123 | 675 | 510 | 93.6 | 0.7 | 2.6 | 3.2 |
| Comparative Example 4 | 114 | 508 | 400 | 90.1 | 1.2 | 5.2 | 3.5 |
| Comparative Example 5 | 119 | 850 | 600 | 91.2 | 1.1 | 3.8 | 3.8 |

| | Functional group quantity | -AIBA adsorbed quantity | | Pore volume | |
|---|---|---|---|---|---|
| | Total acidic group content [meq/g] | 24 hours [mg/g] | 3 hours [mg/g] | 20-15,000 nm [mL/g] | 7.5-15,000 [mL/g] |
| Working Example 1 | 0.13 | 5.74 | — | 0.04 | 0.10 |
| Working Example 2 | 0.21 | 5.35 | — | 0.14 | 0.30 |
| Working Example 3 | 0.21 | 7.88 | — | 0.49 | 0.55 |
| Working Example 4 | 0.21 | 7.36 | 4.86 | 0.09 | 0.13 |
| Working Example 5 | 0.24 | 7.95 | — | 0.33 | 0.39 |
| Working Example 6 | 0.27 | 6.62 | — | 0.69 | 0.73 |
| Working Example 7 | 0.31 | 9.30 | — | 0.19 | 0.28 |
| Working Example 8 | 0.20 | 9.77 | — | 0.54 | 0.56 |
| Working Example 9 | 0.17 | 8.89 | — | 0.50 | 0.51 |
| Working Example 10 | 0.14 | 9.25 | — | 0.30 | 0.30 |
| Working Example 11 | 0.24 | 9.20 | — | 0.37 | 0.41 |
| Working Example 12 | 0.23 | 11.05 | — | 0.02 | 0.04 |
| Working Example 13 | 0.15 | 8.18 | — | 0.40 | 0.43 |
| Working Example 14 | 0.11 | 5.46 | — | 0.04 | 0.05 |
| Working Example 15 | 0.13 | 7.16 | — | 0.05 | 0.07 |
| Working Example 16 | 0.17 | 9.02 | — | 0.06 | 0.08 |
| Working Example 17 | 0.18 | 8.44 | 4.56 | 0.06 | 0.08 |
| Working Example 18 | 0.26 | 8.51 | — | 0.12 | 0.19 |
| Working Example 19 | 0.18 | 8.20 | — | 0.25 | 0.29 |
| Working Example 20 | 0.21 | 8.60 | 5.28 | 0.14 | 0.18 |
| Working Example 21 | 0.23 | 7.47 | 3.29 | 0.09 | 0.14 |
| Working Example 22 | 0.21 | 5.80 | 2.68 | 0.06 | 0.12 |
| Working Example 23 | 0.20 | 6.62 | 0.58 | 0.07 | 0.18 |
| Working Example 24 | 0.15 | 7.13 | 4.07 | 0.09 | 0.11 |
| Working Example 25 | 0.18 | 7.49 | 4.15 | 0.07 | 0.10 |
| Working Example 26 | 0.21 | 7.75 | 4.22 | 0.05 | 0.08 |
| Working Example 27 | 0.13 | 6.46 | 1.34 | 0.07 | 0.14 |
| Comparative Example 1 | 0.21 | 2.25 | — | 0.03 | 0.08 |
| Comparative Example 2 | 0.11 | 2.01 | — | 0.02 | 0.04 |
| Comparative Example 3 | 0.14 | 1.81 | — | 0.27 | 0.28 |
| Comparative Example 4 | 0.05 | 0.00 | — | 0.03 | 0.04 |
| Comparative Example 5 | 0.10 | 1.90 | — | 0.04 | 0.05 |

Figure 1:
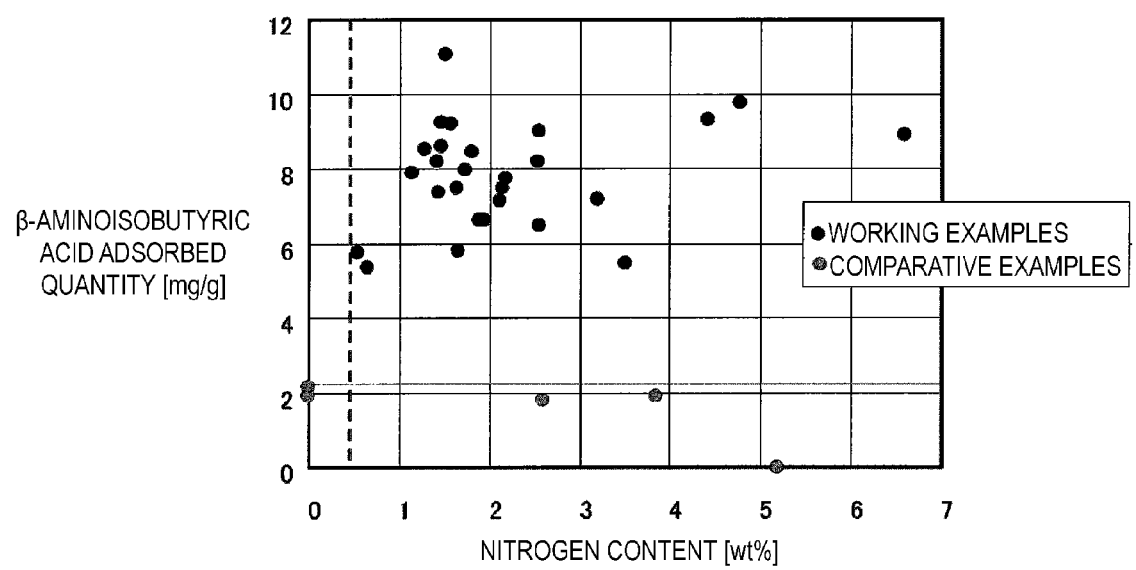
FIG. 1 is a graph showing the -aminoisobutyric acid adsorbed quantity (24 hours) of orally administered adsorbents obtained in working examples and comparative examples.

As is clear from Table 1 and FIG. 1, the spherical activated carbon of Working Examples 1 to 27, in which the nitrogen content was not less than 0.5 wt %, had a far superior -aminoisobutyric acid adsorbed quantity (24-hours) than Comparative Examples 1 and 2, in which the nitrogen content was 0 wt %.

FIG. 2 illustrates the relationship between nitrogen content and -aminoisobutyric acid adsorbed quantity (24 hours) for spherical activated carbon having a BET specific surface area of approximately 1600 m$^2$/g and spherical activated carbon having a BET specific surface area of approximately 1200 m$^2$/g. As the nitrogen content increased, the -aminoisobutyric acid adsorbed quantity increased. In particular, it is seen that at relatively low nitrogen content from 0.5 wt % to 3 wt %, nitrogen content and -aminoisobutyric acid adsorbed quantity correlate, and nitrogen content influences -aminoisobutyric acid adsorbed quantity.

FIG. 3 illustrates the association between a BET specific surface area and -aminoisobutyric acid adsorbed quantity. As is clear from FIG. 3, when the BET specific surface area is not less than 700 m$^2$/g, the increase in -aminoisobutyric acid adsorbed quantity is remarkable.

FIG. 4 illustrates the relationship between average particle size and -aminoisobutyric acid adsorbed quantity (3 hours) for spherical activated carbon having a BET specific surface area of approximately 1600 m$^2$/g and spherical activated carbon having a BET specific surface area of approximately 1200 m$^2$/g. As is clear from FIG. 4, when average particle size was from 50 to 200 μm, the -aminoisobutyric acid adsorbed quantity (3-hour) increased. In short, it is thought that the initial adsorption ability in the body is excellent.

INDUSTRIAL APPLICABILITY

The orally administered adsorbent of the present invention may be used as an orally administered adsorbent for therapy or prophylaxis of a renal disease or may be used as an adsorbent for therapy or prophylaxis of a hepatic disease.

Examples of the renal disease include chronic renal failure, acute renal failure, chronic pyelonephritis, acute pyelonephritis, chronic nephritis, acute nephritic syndrome, acute progressive nephritic syndrome, chronic nephritic syndrome, nephrotic syndrome, nephrosclerosis, interstitial nephritis, tubulopathy, lipoid nephrosis, diabetic nephropathy, renovascular hypertension, and hypertension syndrome, or secondary renal diseases attendant to these primary diseases. Another example is pre-dialysis mild renal failure, and it may be used in condition improvement of mild renal failure before dialysis or condition improvement during dialysis (see "Clinical Nephrology," Asakura Publishing, N. Honda, K. Koiso, K. Kurogawa, 1990 edition, and "Nephrology," Igaku Shoin, T. Onomae, S. Fujimi, editors, 1981 edition).

Examples of the hepatic disease include fulminant hepatitis, chronic hepatitis, viral hepatitis, alcoholic hepatitis, hepatic fibrosis, cirrhosis, hepatic cancer, autoimmune hepatitis, drug-induced allergic hepatitis, primary biliary cirrhosis, tremor, encephalopathy, metabolic disorder, and functional disorder. Otherwise, it may also be used in therapy of illnesses caused by poisonous substances present in the body, namely psychiatric disorder and the like.

The present invention was described above using specific modes of embodiment, but modifications and improvements apparent to persons having ordinary skill in the art are also included in the scope of the present invention.

The invention claimed is:

1. An orally administered adsorbent comprising spherical activated carbon,
    wherein the spherical activated carbon is composed of carbon, hydrogen, nitrogen, and oxygen atoms,
    wherein the nitrogen atom content is not less than 0.5 wt % and not more than 4.4 wt %, and the carbon atom content is not less than 88.2 wt % and not more than 95.7 wt %, of the spherical activated carbon,
    wherein a specific surface area determined by the Brunauer-Emmett-Teller (BET) method of spherical activated carbon is 700 $m^2/g$ to 3000 $m^2/g$, and
    wherein the average particle size of the spherical activated carbon is 0.01 mm to 1 mm.

2. The orally administered adsorbent according to claim 1, wherein the average particle size of the spherical activated carbon is from 50 to 200 μm.

3. The orally administered adsorbent according to claim 1, wherein the spherical activated carbon is prepared using a thermoplastic resin, thermosetting resin, or ion exchange resin that contains nitrogen atoms as a carbon source.

4. The orally administered adsorbent according to claim 3, wherein the thermoplastic resin or ion exchange resin contains a monomer selected from the group consisting of acrylonitrile, ethylacrylonitrile, methylacrylonitrile, diphenylacrylonitrile, and chloroacrylonitrile.

5. The orally administered adsorbent according to claim 3, wherein the thermosetting resin contains a monomer selected from the group consisting of melamine and urea.

6. A therapeutic or prophylactic agent for a renal disease containing as an active ingredient the orally administered adsorbent described in claim 1.

7. A therapeutic or prophylactic agent for a hepatic disease containing as an active ingredient the orally administered adsorbent described in claim 1.

* * * * *